US011534401B2

(12) United States Patent
Kelly et al.

(10) Patent No.: US 11,534,401 B2
(45) Date of Patent: Dec. 27, 2022

(54) THERMO-RESPONSIVE HYDROGEL FOR INTRATUMORAL ADMINISTRATION AS A TREATMENT IN SOLID TUMOR CANCERS

(71) Applicant: Royal College of Surgeons in Ireland, Dublin (IE)

(72) Inventors: Helena Kelly, Dublin (IE); Garry Duffy, Dublin (IE); Seona Rossi, Dublin (IE); Conn Hastings, Dublin (IE)

(73) Assignee: THE ROYAL COLLEGE OF SURGEONS IN IRELAND, Dublin (IE)

( * ) Notice: Subject to any disclaimer, the term of this patent is extended or adjusted under 35 U.S.C. 154(b) by 0 days.

(21) Appl. No.: 16/762,138

(22) PCT Filed: Nov. 7, 2018

(86) PCT No.: PCT/EP2018/080518
§ 371 (c)(1),
(2) Date: May 6, 2020

(87) PCT Pub. No.: WO2019/092049
PCT Pub. Date: May 16, 2019

(65) Prior Publication Data
US 2020/0360281 A1 Nov. 19, 2020

(30) Foreign Application Priority Data
Nov. 7, 2017 (EP) .................................... 17200449

(51) Int. Cl.
| | |
|---|---|
| *A61K 9/06* | (2006.01) |
| *A61K 31/337* | (2006.01) |
| *A61K 31/352* | (2006.01) |
| *A61K 31/7068* | (2006.01) |
| *A61K 33/243* | (2019.01) |
| *A61K 47/10* | (2017.01) |
| *A61K 47/22* | (2006.01) |
| *A61K 47/36* | (2006.01) |
| *A61K 47/40* | (2006.01) |
| *A61K 9/00* | (2006.01) |
| *A61K 9/19* | (2006.01) |
| *A61K 47/38* | (2006.01) |

(52) U.S. Cl.
CPC .............. *A61K 9/06* (2013.01); *A61K 31/337* (2013.01); *A61K 31/352* (2013.01); *A61K 31/7068* (2013.01); *A61K 33/243* (2019.01); *A61K 47/10* (2013.01); *A61K 47/22* (2013.01); *A61K 47/36* (2013.01); *A61K 47/40* (2013.01); *A61K 9/0024* (2013.01); *A61K 9/19* (2013.01)

(58) Field of Classification Search
None
See application file for complete search history.

(56) References Cited

U.S. PATENT DOCUMENTS 3,740,421 A 6/1973 Schmolka
2016/0375177 A1* 12/2016 Hauser .................. A61K 38/06
424/93.7

FOREIGN PATENT DOCUMENTS

CN 105778126 A * 7/2016

OTHER PUBLICATIONS

Machine-translation for CN 105778126A (Year: 2016).*
Jordan ("An Investigation of the Cytotoxicity of a Novel Thermoresponsive Gel for use in Injectable Intratumoral Cancer Therapy", The Undergraduate Journal, vol. 4(3) (2012). (Year: 2012).*
International Search Report and Written Opinion for Int'l Application No. PCT/EP2018/080518, titled: A Thermo-Responsive Hydrogel for Infratumoral Administration as a Treatment in Solid Tumor Cancers, dated Jan. 16, 2019.
Bonacucina et al., "Effect of hydroxypropyl beta-cyclodextrin on the self-assembling and thermogelation properties of Poloxamer 407," *Eur J Pharm Sci.*, 32: 115-122 (2007).
Chen et al., "Mechanical, Rheological and Release Behaviors of a Poloxamer 407/Poloxamer 188/Carbopol 940 Thermosensitive Composite Hydrogel," *Molecules*, 18(10): 12415-12425 (2013).
Cho et al., "Poloxamer/Cyclodextrin/Chitosan-Based Thermoreversible Gel for Intranasal Delivery of Fexofenadine Hydrochloride," *J Pharm Sci*, 100(2): 681-691 (2011).
Fatimi et al., "A new injectable radiopaque chitosan-based sclerosing embolizing hydrogel for endovascular therapies," *Acta Biomater*, 8(7): 2712-2721 (2012).
Fridman et al., "Increased initiation and growth of tumor cell lines, cancer stem cells and biopsy material in mice using basement membrane matrix protein (Cultrex or Matrigel) co-injection," *Nat Protoc*, 7(6): 1138-1144 (2012).
Invitrogen. (2004). Live/Dead® Viability/Cytotoxicity Kit for Mammalian Cells Protocol. Retrieved from Internet on: Aug. 10, 2021, Retrieved from Internet at: https://www.thermofisher.com/ie/en/home/references/protocols/cell-and-tissue-analysis/protocols/live-dead-viability-cytotoxicity-kit-for-mammalian-cells.html.
Jordan, "An Investigation of the Cytotoxicity of a Novel Thermo-Responsive Gel for Use in Injectable Intratumoral Cancer Therapy," *The Undergraduate Journal*, vol. 4: p. 286-309 (2012).

(Continued)

*Primary Examiner* — Sin J Lee
(74) *Attorney, Agent, or Firm* — Hamilton, Brook, Smith & Reynolds, P.C.

(57) ABSTRACT

A room temperature injectable thermo-responsive hydrogel comprises a P407 poloxamer base hydrogel, chitosan, 2-Hydroxypropyl β-cyclodextrin and genipin. The chitosan and genipin form an interpenetrating scaffold within the hydrogel in which the chitosan is crosslinked with genipin. Chemotherapeutic drugs can be added to the hydrogel singly or in combination in effective amounts without any loss of thermo-responsiveness in the hydrogel. Therapeutic use of the thermo-responsive hydrogel in the intratumoural treatment of solid cancer is also described.

12 Claims, 19 Drawing Sheets

(56) References Cited

OTHER PUBLICATIONS

Ma et al., "PLK1shRNA and doxorubicin co-loaded thermosensitive PLGA-PEG-PLGA hydrogels for osteosarcoma treatment," *Biomaterials*, 35(30): 8723-8734 (2014).

Tomayko et al., "Determination of subcutaneous tumor size in athymic (nude) mice," *Cancer Chemother Pharmacol*, 24(3): 148-154 (1989).

Cho et al., "Hydrotropic agents for study of in vitro paclitaxel release from polymeric micelles," *Journal of Controlled Release* 97: 249-257 (2004).

Kuang et al., "Long-Term Outcome of Percutaneous Ablation in Very Early-Stage Hepatocellular Carcinoma," *J Gastrointest Surg* 15: 2165-2171 (2011).

Lin et al., "Randomised controlled trial comparing percutaneous radiofrequency thermal ablation, percutaneous ethanol injection, and percutaneous acetic acid injection to treat hepatocellular carcinoma of 3 cm or less," *Gut*; 54: 1151-1156 (2005).

International Preliminary Report on Patentability for Int'l Application No. PCT/EP2018/080518, titled: A Thermo-Responsive Hydrogel for Intratumoral Administration as a Treatment in Solid Tumor Cancers, dated May 12, 2020.

\* cited by examiner

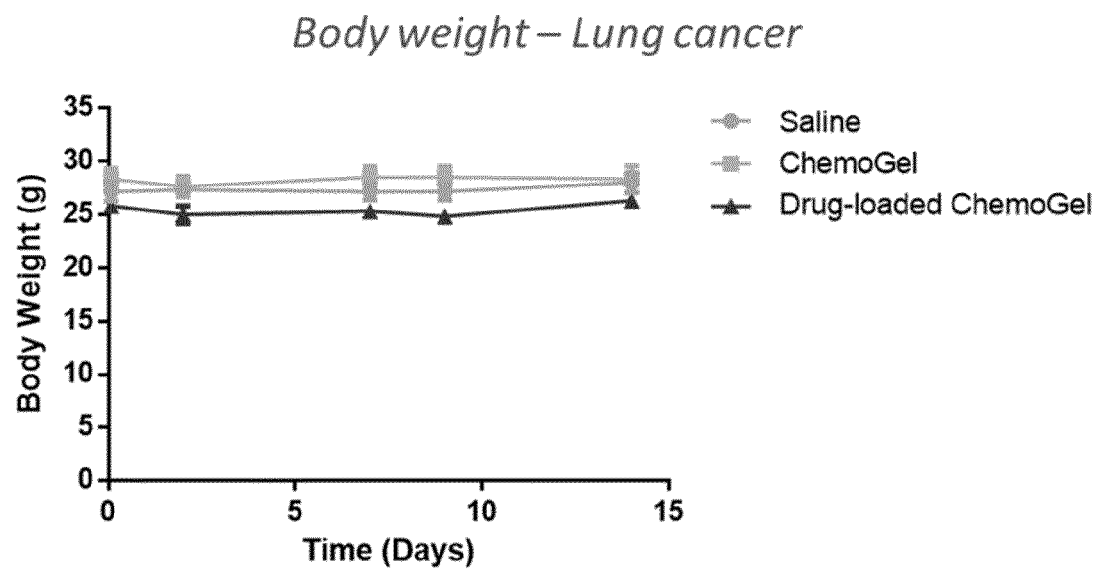
Figure 16A(1)
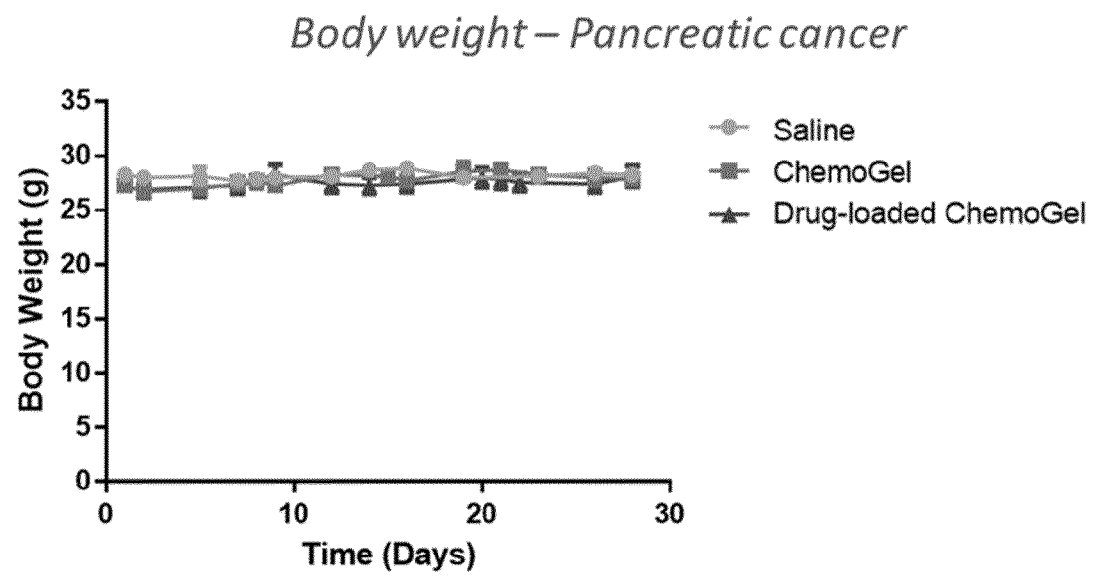
Figure 16A(2)

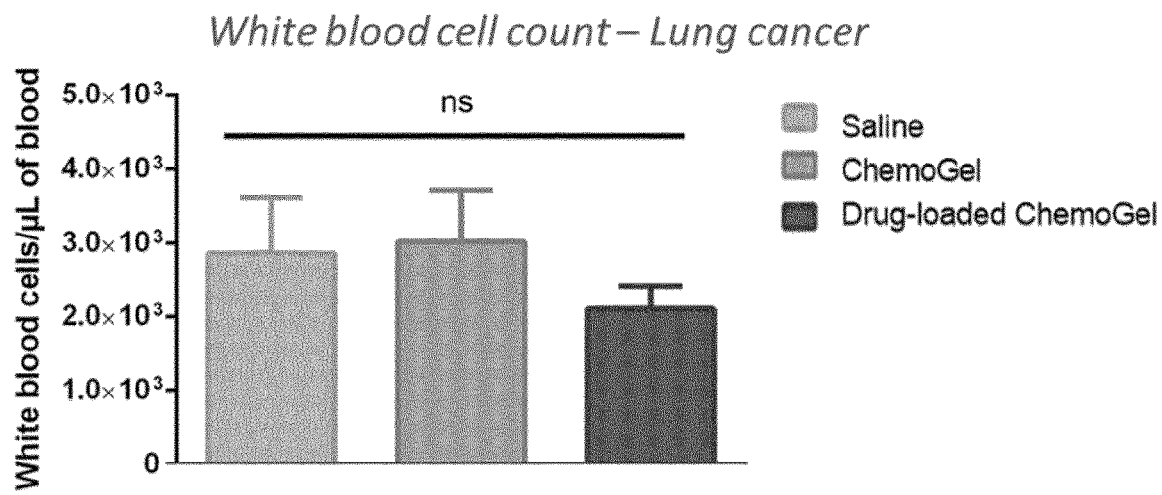
Figure 16B(1)
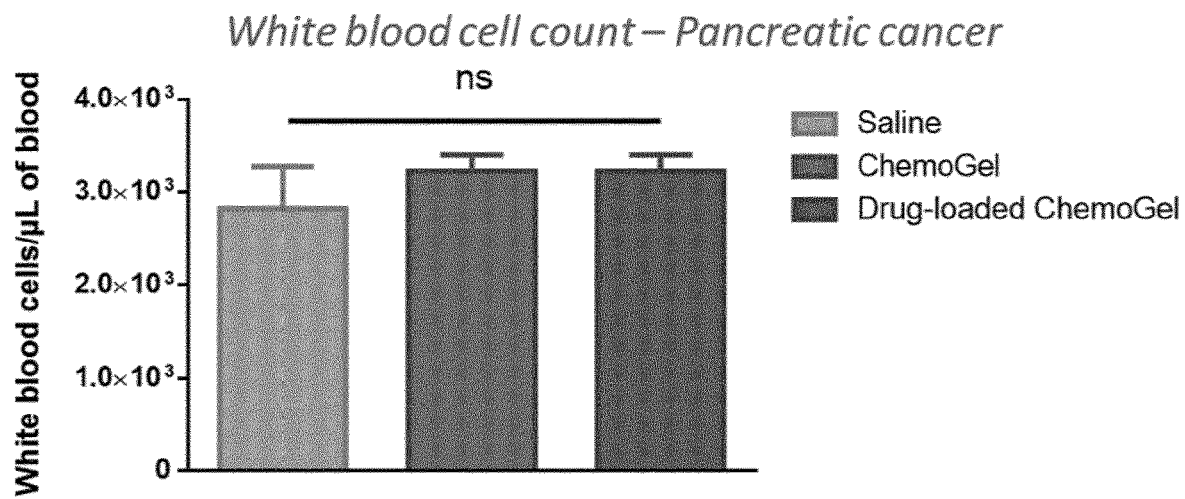
Figure 16B(2)

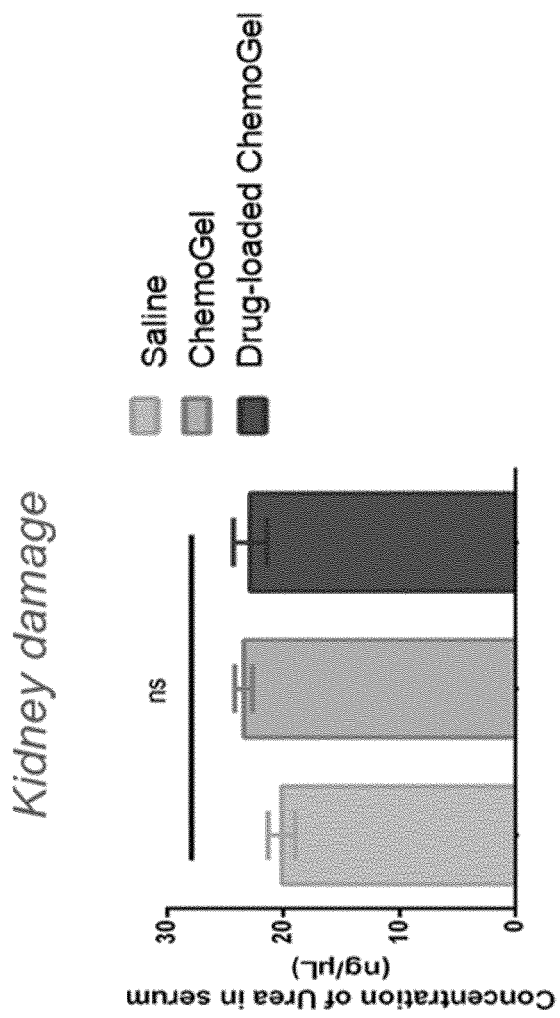
Figure 16C(2)
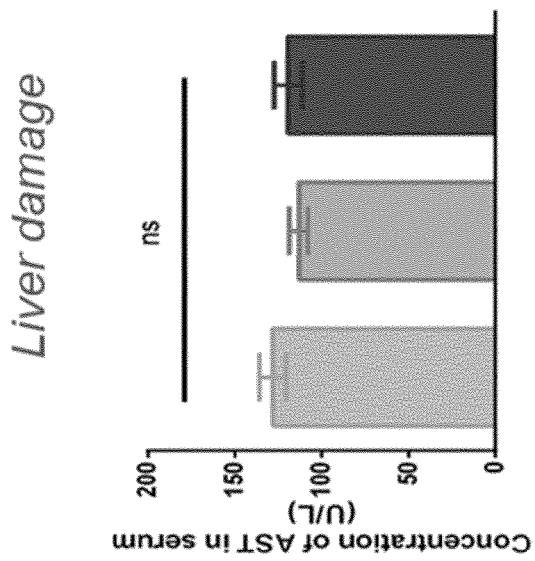
Figure 16C(1)

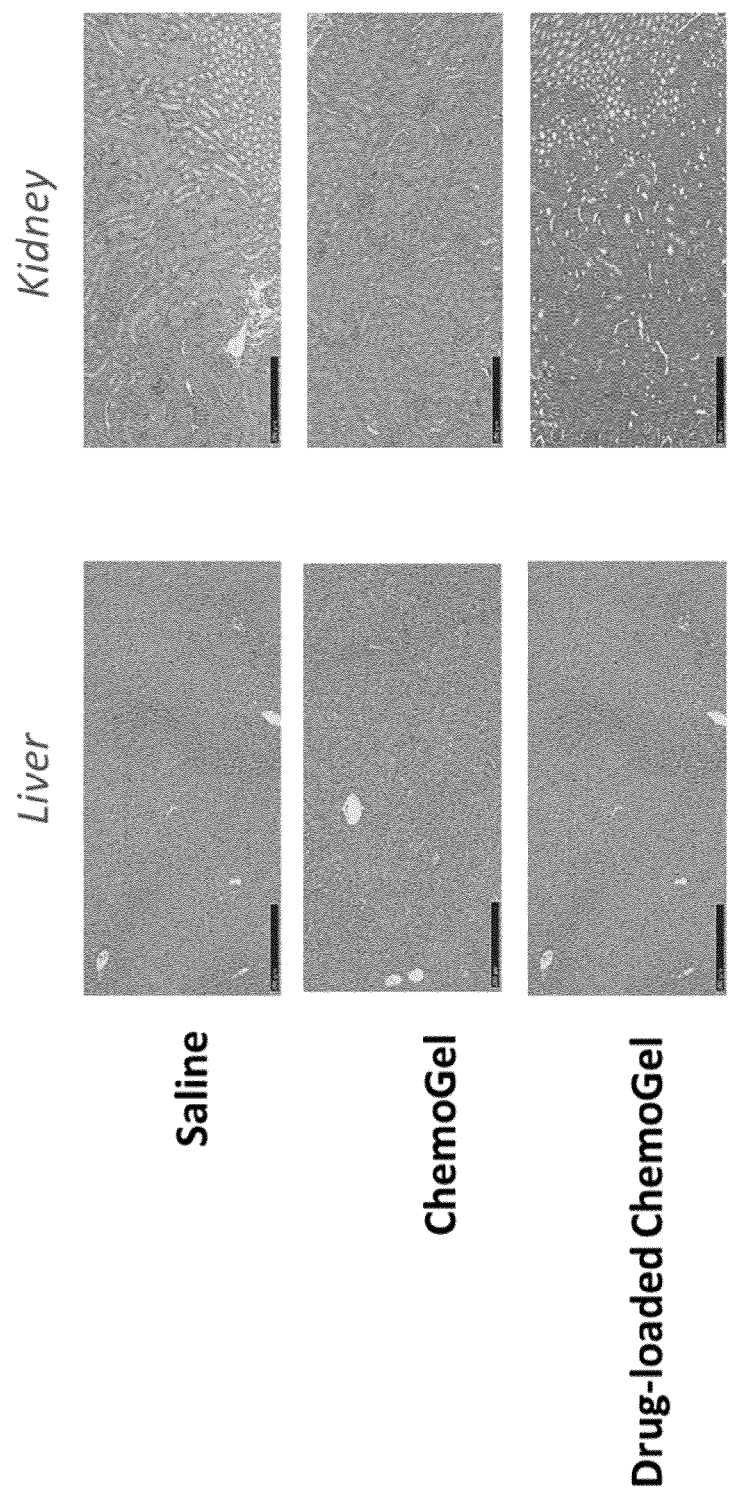
Figure 16D(2)
Figure 16D(1)

THERMO-RESPONSIVE HYDROGEL FOR INTRATUMORAL ADMINISTRATION AS A TREATMENT IN SOLID TUMOR CANCERS

This application is the U.S. National Stage of International Application No. PCT/EP2018/080518, filed Nov. 7, 2018, which designates the U.S., published in English, and claims priority under 35 U.S.C. § 119 or 365(c) to EP Application No. 17200449.1, filed Nov. 7, 2017. The entire teachings of the above applications are incorporated herein by reference.

FIELD OF THE INVENTION

The present invention relates to a thermo-responsive hydrogel. Also contemplated are methods of treating proliferative disorders by intratumoral administration of a thermo-responsive polymer solution.

BACKGROUND TO THE INVENTION

Systemic chemotherapy, in conjunction with radiation and surgery is the most common approach to treatment for a range of solid cancers. However systemic chemotherapy is generally associated with a range of toxic, off-site side effects e.g. immunosuppression and organ damage, which in many cases can be dose limiting. The reduction in quality of life during traditional chemotherapeutic treatment due to off target side effects is well documented, resulting in physical, psychological and social implications for the patient. When systemically administered chemotherapeutics reach the target site, penetration into the tumour mass is difficult to achieve due to the altered Tumour Micro Environment (TME). The three dimensional architecture of a tumour can determine the response to systemic chemotherapy. Drug must access as many viable cells within the tumour as possible in a sufficient concentration to exert significant cytotoxicity. However, this can be hampered by aberrant vascular growth and erratic tumour blood flow. This can also result in areas of acidity and hypoxia within the tumour. The intracellular pH of a tumour can vary from neutral to alkaline, while the extracellular pH is typically lower than normal tissues, meaning weakly basic, positively-charged drugs such as doxorubicin can display poor cellular uptake as a result of poor membrane permeability. Furthermore, raised interstitial pressure at the tumour core can result in poor tissue infiltration of drug molecules. Given the inherent complexity and physiological barriers of the TME that a systemically administered drug molecule must surmount to reach its target and exert an effect via conventional intravenous chemotherapy, more targeted and controllable approaches are required.

Direct injection of chemotherapeutics in saline solution into the tumour mass (IT instillation) has been explored as a way of achieving more targeted delivery of chemotherapeutics to the site of action. However the direct IT instillation of chemotherapeutic solutions is limited by the rapid clearance of these drugs from the tumour site, which results in inaccurate and unpredictable dosing, and toxicity in surrounding tissue.

Therefore attention has turned to the development of drug delivery systems which can facilitate retention within the tumour and controlled release of chemotherapeutics from inside the tumour. Intratumoural administration of chemotherapeutics incorporated in thermo-responsive hydrogels can confer a localised and sustained release of drug directly within the tumour, potentially negating the need for repeated dosing. Since such hydrogels are directly implantable in the target tissue, they may help to circumvent TME barriers to tissue penetration and reduce non-target tissue exposure and rapid drug clearance associated with systemic delivery and IT instillation.

However while interest in thermo-responsive hydrogels for intratumoural delivery has been significant, inaccessibility to treatment of sites, inability to image after delivery, along with challenges related to their often rapid disintegration at their site of action, and poor ability to solubilise non-aqueous drug systems has in the past limited their translational progress.

There are a limited number of systems currently available which seek to address the problem of loco-regional chemotherapeutic drug delivery. The majority of products currently available are focused on the treatment of Hepatic Cellular Carcinoma (HCC) and colorectal liver metastases through the use of combined drug delivery and embolization approaches. This involves the placement of a catheter in the tumour-supplying arteries, which arise from the main hepatic artery with a view to delivering an embolic agent +/− chemotherapeutic drug to cut off blood supply to the tumour mass, which will result in ischemia and cell death (intra-arterial therapy), also known as TAE (transarterial embolization) or TACE (transarterial chemoembolization). The liver is a well vascularised organ, and as such, other blood vessels can maintain adequate blood supply to the rest of the healthy tissue. Embolic agents commonly used include iodised oil (Lipiodol) and Embolisation Beads e.g. DC/DC Lumi beads, Life Pearl Microspheres which can then be loaded with drugs e.g. doxorubicin, iritonetacan or gamma emitting agents e.g. Ytrrium. This may be a limiting factor in the translation of this technique to other tumours, as a well vascularised organ is required to ensure that healthy tissue is not compromised.

Another loco-regional drug delivery system is Gliadel wafers which are wafers used to deliver the chemotherapeutic drug carmustine to the resection site of glioblastoma patients. While these approaches focus on loco-regional drug delivery of chemotherapeutic drugs the formulation type is markedly different from the proposed invention in all cases.

However there has been significant interest in thermo-responsive hydrogel drug delivery systems, with increasing numbers of publications in recent years.

A number of these publications look at combinations of poloxamer with chitosan, and/or cyclodextrins, and/or chemotherapeutic drugs. (Cho et al., 2011) describes a Poloxamer 407/HP-β-CD/Chitosan formulation for the delivery of fexofenadine HCl. However the formulation differed in final components (absence of genipin), its overall composition, and the method of manufacture. (Fatimi et al., 2012) explored the potential of using a thermosensitive hydrogel in combination with an imaging agent as an endovascular embolising agent, however the thermo-responsive hydrogel system used was based on chitosan/GP.

Jordan et al. describe a thermo-responsive hydrogel for a potential application as an injectable intratumoral delivery platform, comprising poloxamer P407, chitosan, HR-CD and genipin. The polymer solution required curing at 37° C. for 24 hours to initiate the crosslinking action of genipin required to retard the dissolution of the gel. After curing for 24 h, the polymer solution showed a sol-gel transition at approx. 25° C. The sol-gel transition temperature of 25° C. was problematical as it could lead to gelation after formulation but prior to delivery in warmer environments, and would be prone to gelate too rapidly and prematurely during clinical delivery. In addition, on addition of chemotherapeutic agents (cisplatin), the hydrogel lost clinically relevant thermoresponsivity. While the storage problems of the hydrogel could be overcome by providing the polymer solution in a lyophilised format, and re-hydrating prior to use in surgery, the requirement to have to cure the re-hydrated polymer solution for 24 hours prior to use to activate cross-linking is not practical for a clinical situation.

It is an object of the invention to overcome at least one of the above-referenced problems.

SUMMARY OF THE INVENTION

The Applicant has discovered that the hydrogel of Jordan et al. is improved by reduction of the level of genipin, typically to less than 0.2% (w/w). In particular, this change provides a hydrogel with a clinically translatable sol-gel transition temperature (for example 28-30° C.—see hydrogels GF3 and GF5 compared with hydrogels GF1, GF2 and GF4 Table 1), making the hydrogel more suitable for storage and injectability in a clinical setting, and providing a hydrogel that does not require a curing period and yet retains thermoresponsivity (FIG. 2 and Table 1). This makes the hydrogel ideal for a clinical setting, where the polymer solution can be provided in a lyophilised format, and re-hydrated in the hospital environment, for immediate use without the requirement for a 24-hour curing period. In addition, in-vivo intratumoural studies have surprisingly shown that a hydrogel according to the invention was retained at site of injection for 14 days (FIG. 14), caused significant reduction in tumour volume increase (FIG. 15), and did not cause acute off-site toxicity in the mouse for up to 14 days (FIG. 16). In addition, chemotherapeutic agents can optionally be added to the hydrogel of the invention while maintaining a clinically relevant thermoresponsivity (FIGS. 17 and 18).

In one embodiment, the level of poloxamer is reduced below 20% (w/w), for example 17%. This results in the storage modulus G' being increased to above 10,000 Pa, which provides a more robust gel in-vivo, leading to enhanced persistence of the gel in a tumour (Table 1, FIG. 14) and in-turn a reduction in tumour volume increase (FIG. 15).

According to a first aspect of the present invention, there is provided a hydrogel comprising:
a thermo-responsive base hydrogel (i.e. a poloxamer polymer),
a hydrogel strengthening agent (i.e. chitosan),
optionally an inclusion complexer (i.e. a β-cyclodextrin such as 2-Hydroxypropyl R-cyclodextrin (HP-β-CD)),
genipin, and
an aqueous base.
In one embodiment, the hydrogel comprises:
15-25% thermo-responsive base hydrogel (i.e. a poloxamer polymer),
a hydrogel strengthening agent (i.e. chitosan),
optionally an inclusion complexer (i.e. a β-cyclodextrin such as 2-Hydroxypropyl β-cyclodextrin (HP-β-CD)),
0.05 to 0.25% genipin, and
an aqueous base.
In one embodiment, the hydrogel is room temperature injectable and comprises:
15-18% thermo-responsive base hydrogel (i.e. a poloxamer polymer),
a hydrogel strengthening agent (i.e. chitosan),
an inclusion complexer (i.e. a β-cyclodextrin such as 2-Hydroxypropyl β-cyclodextrin (HP-β-CD)),
genipin, and
an aqueous base.

At physiological temperatures, the hydrogel strengthening agent forms an interpenetrating scaffold within the thermo-responsive hydrogel in which the hydrogel strengthening agent is crosslinked with genipin.

Typically, the hydrogel is a thermo-responsive hydrogel. Typically, the hydrogel is uncured.

In one embodiment, the hydrogel strengthening agent is selected from methyl cellulose, dextan, carrageenan, chitosan, and pluronic R.

In one embodiment, the hydrogel strengthening agent is chitosan.

In one embodiment, the chitosan forms an interpenetrating scaffold within the hydrogel in which the chitosan is crosslinked with genipin.

In one embodiment, the poloxamer is poloxamer 407, optionally in combination with an additional poloxamer such as poloxamer 188.

In one embodiment, a thermo-responsive base hydrogel comprises poloxamer and an inclusion complexer, for example a cyclodextrin. In one embodiment, the inclusion complexer is a β-cyclodextrin, for example 2-Hydroxypropyl β-cyclodextrin.

In one embodiment, the thermo-responsive hydrogel comprises an active agent. In one embodiment, the active agent is one or more chemotherapeutic agents. In one embodiment, the active agent is a cell. In one embodiment, the active agent is an antibody, such as a monoclonal antibody, or an antibody fragment. In one embodiment, the active agent is a nucleic acid (optionally provided as part of a nucleic acid vector such as a plasmid).

In one embodiment, the chemotherapeutic agents is water soluble. In one embodiment, the chemotherapeutic agents is poorly water soluble.

In one embodiment, the chemotherapeutic agent is dispersed within the hydrogel in the form of an inclusion complex comprising chemotherapeutic agent and an inclusion complexer such as 2-Hydroxypropyl β-cyclodextrin.

In one embodiment, the thermo-responsive hydrogel comprises a contrast agent. In one embodiment, the contrast agent is an iodinated contrast agent.

In one embodiment, the hydrogel is liquid (i.e. injectable) at room temperature (i.e. 18-23° C.).

In one embodiment, the hydrogel is solid or semi-solid at body temperature (24-37° C.).

In one embodiment, the thermo-responsive hydrogel comprises poloxamer polymer (w/w), typically 15-25%. In one embodiment, the thermo-responsive hydrogel comprises 17-22% thermo-responsive polymer (w/w). In one embodiment, the thermo-responsive hydrogel comprises up to 19% poloxamer polymer, for example 15-19%, 15-18% or 16-18% or about 17% poloxamer polymer (w/w). In one embodiment, the poloxamer polymer is provided in an aqueous base. The use of lower levels of poloxamer, for example less than 20%, 19% or 18%, surprisingly provides a hydrogel with a higher storage modulus, which allows the gel persist in-vivo for longer periods, for example up to 14 days.

In one embodiment, the thermo-responsive hydrogel comprises 0.1-1.0% gel strengthening agent (i.e. chitosan) (w/w). In one embodiment, the thermo-responsive hydrogel comprises 0.3-0.5% gel strengthening agent (i.e. chitosan) (w/w).

In one embodiment, the thermo-responsive hydrogel comprises 5-20% inclusion complexer (w/w). In one embodiment, the thermo-responsive hydrogel comprises 8-15% inclusion complexer (i.e. 2-Hydroxypropyl β-cyclodextrin) (w/w).

In one embodiment, the thermo-responsive hydrogel comprises 0.05-2.0% genipin (w/w). In one embodiment, the thermo-responsive hydrogel comprises 0.05-0.3% genipin (w/w). In one embodiment, the thermo-responsive hydrogel comprises 0.5-0.2% genipin (w/w). In one embodiment, the thermo-responsive hydrogel comprises 0.05-0.15% genipin (w/w). In one embodiment, the thermo-responsive hydrogel comprises about 0.1% genipin (w/w).

In one embodiment, the thermo-responsive hydrogel comprises 0.01 to 10% chemotherapeutic agent (w/w). In one embodiment, the thermo-responsive hydrogel comprises 0.1 to 5% chemotherapeutic agent (w/w). In one embodiment, the thermo-responsive hydrogel comprises 0.1 to 1.0% chemotherapeutic agent (w/w). In one embodiment, the thermo-responsive hydrogel comprises 1.0 to 5.0% chemotherapeutic agent (w/w).

In one embodiment, the thermo-responsive hydrogel has a storage modulus G' of at least 8,000 Pa at 37° C. In one embodiment, the thermo-responsive hydrogel has a storage modulus G' of at least 9,000 Pa at 37° C. In one embodiment, the thermo-responsive hydrogel has a storage modulus G' of at least 10,000 Pa at 37° C. In one embodiment, the thermo-responsive hydrogel has a storage modulus G' of at least 11,000 Pa at 37° C.

In one embodiment, the thermo-responsive hydrogel comprises contrast agent, for example about 1-10% contrast agent (w/w). In one embodiment, the thermo-responsive hydrogel comprises 2-7% contrast agent (w/w). In one embodiment, the contrast agent is an iodinated contrast agent.

In one embodiment, the thermo-responsive hydrogel comprises or consists essentially of:
  a poloxamer;
  an interpenetrating scaffold within the hydrogel comprising chitosan crosslinked with 0.05 to 0.15% genipin (w/w);
  a β-cyclodextrin;
  one or more chemotherapeutic agents;
  optionally a contrast agent; and
  an aqueous base.

In one embodiment, the thermo-responsive hydrogel comprises or consists essentially of:
  15-25% poloxamer (w/w);
  0.1-1.0% chitosan (w/w);
  0.05-0.15% genipin (w/w);
  5-20% β-cyclodextrin (i.e. 2-Hydroxypropyl β-cyclodextrin) (w/w);
  optionally 1-10% contrast agent (w/w);
  optionally, one or more chemotherapeutic agents; and
  an aqueous base.

In one embodiment, the thermo-responsive hydrogel comprises or consists essentially of:
  15-18% thermo-responsive base hydrogel (w/w);
  0.3-0.7% chitosan (w/w);
  0.05-0.15% genipin (w/w);
  8-15% 2-Hydroxypropyl β-cyclodextrin (w/w);
  1-10% contrast agent (w/w);
  optionally, one or more chemotherapeutic agents; and
  water.

In one embodiment, the thermo-responsive hydrogel comprises or consists essentially of:
  about 17% thermo-responsive base hydrogel (w/w);
  about 0.5% chitosan (w/w);
  about 0.1% genipin (w/w);
  5-20% 2-Hydroxypropyl β-cyclodextrin (w/w);
  1-10% contrast dye (w/w);
  one or more chemotherapeutic agents; and
  an aqueous base.

The invention also provides a thermo-responsive hydrogel according to the invention in a lyophilised form.

The invention also provides a syringe containing a thermo-responsive hydrogel according to the invention.

The invention also provides a thermo-responsive hydrogel according to the invention, for use in a method of treating or preventing a proliferative disorder in a subject.

The invention also provides a thermo-responsive hydrogel according to the invention, for use in a method of treating a solid tumour in a subject, in which the hydrogel is administered intratumorally to the subject or administered to a tumour resection site post-surgical re-section.

The invention also provides a thermo-responsive hydrogel according to the invention, for use in a method of sensitising a solid tumour (or margins of a resected solid tumour) in a subject to the effects of a chemotherapeutic agent.

The thermo-responsive hydrogel of the invention may be used as an intratumoural injectable drug delivery system as an adjunct treatment for tumour burden reduction in a range of solid tumour cancer alone, or in combination with other oncologic treatment approaches e.g. systemic chemotherapy, surgery, radiation treatment. It may also be used in combination with ablative procedures e.g. RFA, MWA, IRE to improve outcomes of treatment. Intratumoural injection of the hydrogel may be achieved using image guided systems and standard minimally invasive procedues such as percutaneous injection, Endoscopic Ultrasound (EUS) or Endobronchial Ultrasound (EBUS). It could also be used to line a resection site after surgery to reduce the likelihood of reoccurrence of tumour growth.

The invention also provides a method of making a thermo-responsive hydrogel comprising the steps of:
  providing a first solution of (for example a β-cyclodextrin such as 2-Hydroxypropyl β-cyclodextrin) and gel strengthening agent (for example chitosan) in an aqueous base;
  cooling the solution to less than 10° C. (preferably less than 6° C.);
  adding thermo-responsive base hydrogel (for example a poloxamer) to the solution and mixing at a temperature of less than 10° C. (preferably less than 6° C.);
  storing the solution at a temperature of less than 10° C. (preferably less than 6° C.) for at least four hours to allow to hydrate; and
  adding genipin to the hydrated solution with stirring for a period of at least four hours to form the thermo-responsive hydrogel; and
  optionally, lyophilising the thermo-responsive hydrogel.

Typically, the process does not include a step of curing the hydrogel.

In one embodiment, the thermo-responsive hydrogel comprises a water soluble chemotherapeutic agent, and the method comprising a step of adding the water soluble chemotherapeutic agent to the first solution. In one embodiment, the water soluble chemotherapeutic agent is dissolved in an aqueous base and added to the first solution.

In one embodiment, the thermo-responsive hydrogel is lyophilised and comprises a water soluble chemotherapeutic agent, the method comprising a step of dissolving the water soluble chemotherapeutic agent in an aqueous base to form an aqueous chemotherapeutic solution, and rehydrating the lyophilised thermo-responsive hydrogel in the aqueous chemotherapeutic solution In one embodiment, the thermo-responsive hydrogel comprises a poorly water soluble chemotherapeutic agent, the method including steps of forming an inclusion complex comprising part of the β-cyclodextrin and the poorly water soluble chemotherapeutic agent, and adding the inclusion complex to the first solution with a remainder of the R-cyclodextrin.

In one embodiment, the inclusion complex is freeze-dried. In one embodiment, about two thirds of the β-cyclodextrin is employed to make the inclusion complex and the remainder is added as free β-cyclodextrin.

In one embodiment, the lyophilised hydrogel is reconstituted in an aqueous solution of active agent, typically an aqueous solution of soluble chemotherapeutic agent.

Other aspects and preferred embodiments of the invention are defined and described in the other claims set out below.

BRIEF DESCRIPTION OF THE FIGURES

FIG. 16. Intratumoural administration of blank or drug-loaded hydrogel (Example 1 GF5, and Examples 4 and 5) did not cause acute off-site toxicity for up to 14 days. A549-uc and Panc-1 tumour bearing mice treated with Saline, hydrogel or drug-loaded hydrogel did not show any significant alterations in body weight (FIG. 16A(1) and FIG. 16A(2)), white blood cell count (FIG. 16B(1) and FIG. 16A(2)) or blood serum levels (FIG. 16C(1) and FIG. 16C(2)) in A549-luc tumour bearing mice of Aspartate transaminase (AST) (left) and Urea (right). Data shown is represented as the mean+SEM (n=6 mice per group). Significance was determined using a one-way ANOVA for (B) and (C). ns=p>0.05. Representative H&E staining of excised liver (left) and kidney (right) tissue day 14 post-intratumoural administration of saline (top), blank hydrogel (middle) or drug-loaded hydrogel (bottom) (FIG. 16D(1) and FIG. 16D(2)).

DETAILED DESCRIPTION OF THE INVENTION

Figure 1:
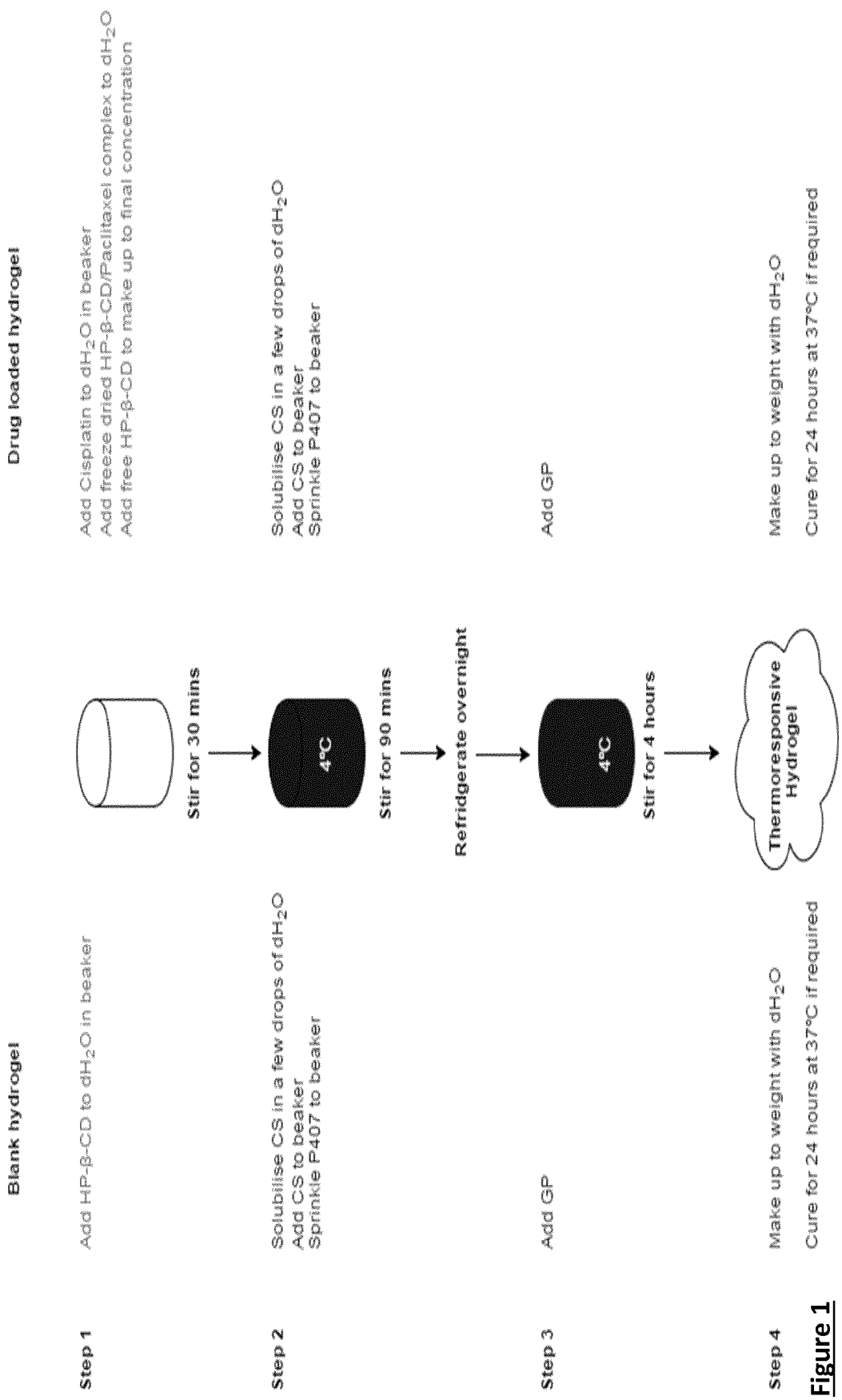
FIG. 1: Schematic outlining formulation Example 1 GF3-5 (left) and Example 4 (right).
Figure 2:
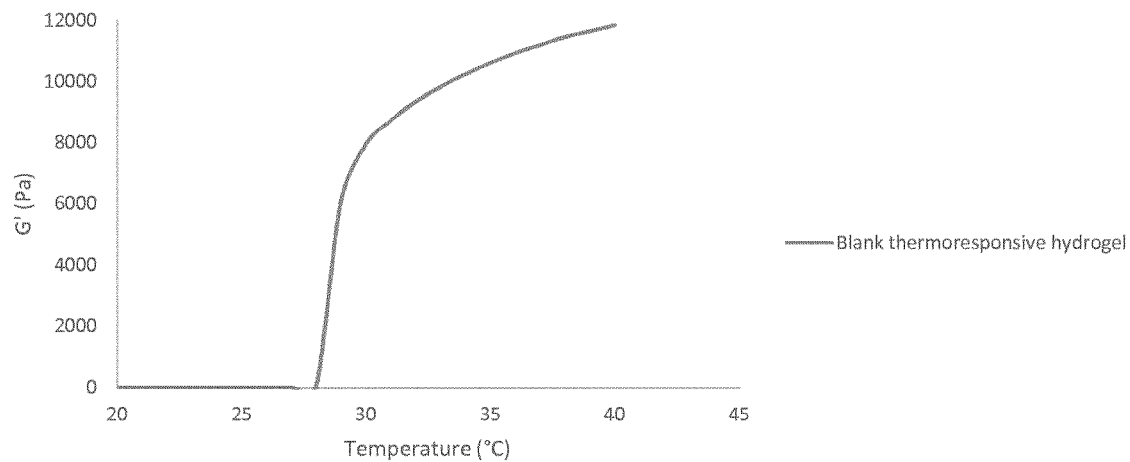
FIG. 2. Rheological temperature response curves (Example 10) obtained used an AR-1000 rheometer (TA Instruments) of blank (non-drug loaded) thermo-responsive hydrogel showing sol-gel transition temperature at 29° C. (formulated according to Example 1 GF5). G' denotes storage modulus.
Figure 3:
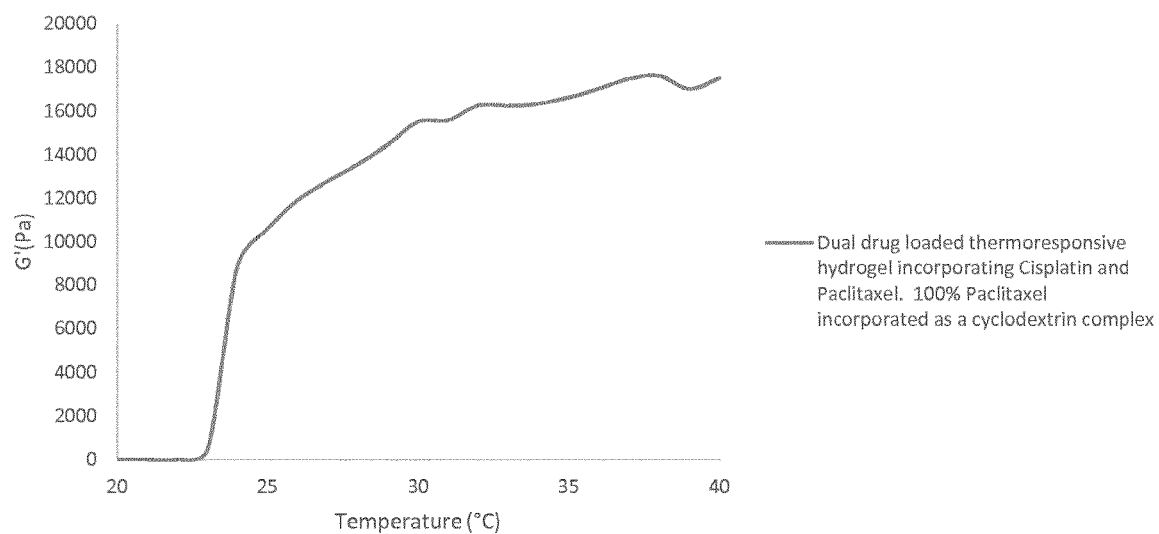
FIG. 3. Rheological temperature response curves (Example 10) obtained used an AR-1000 rheometer (TA Instruments) of thermo-responsive hydrogel drug loaded with Cisplatin and Paclitaxel showing a sol-gel transition at 23° C. (Formulated according to Example 3). Paclitaxel incorporated as a cyclodextrin complex in total concentration of cyclodextrin. G' denotes storage modulus.
Figure 4:
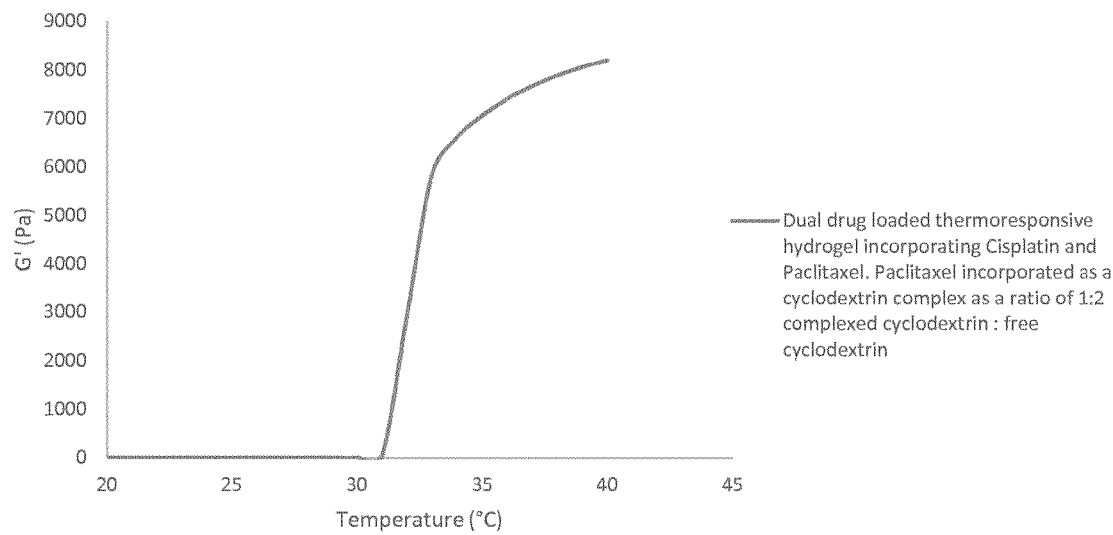
FIG. 4. Rheological temperature response curves (Example 10) obtained used an AR-1000 rheometer (TA Instruments) of thermo-responsive hydrogel drug loaded with Cisplatin and Paclitaxel showing a sol-gel transition at 31° C. (Formulated according to Example 4). Paclitaxel incorporated as a cyclodextrin complex as 33.33% of total cyclodextrin added to the formulation. G' denotes storage modulus.
Figure 5:
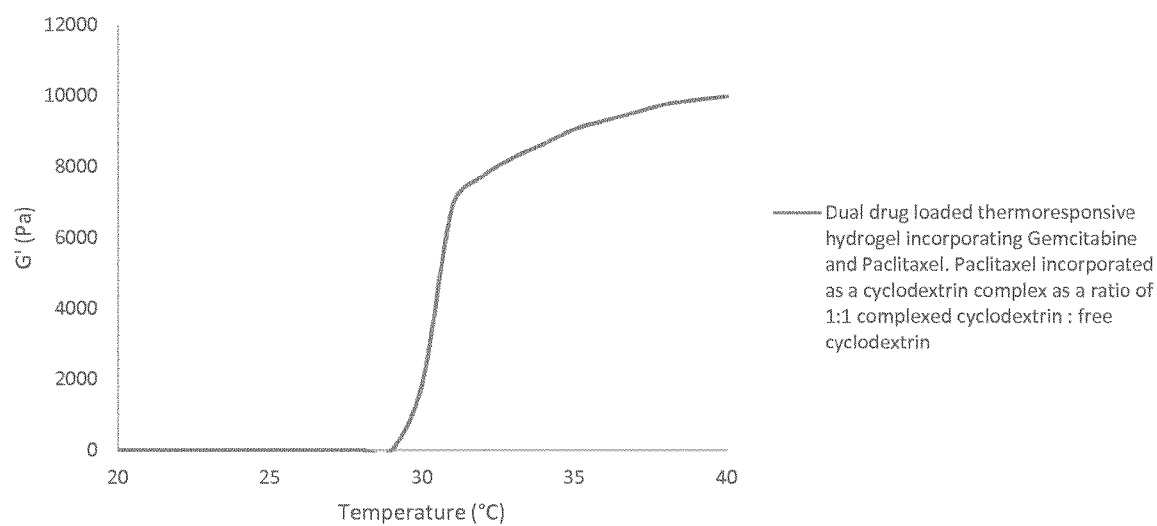
FIG. 5. Rheological temperature response curves (Example 10) obtained used an AR-1000 rheometer (TA Instruments) of thermo-responsive hydrogel drug loaded with gemcitabine and Paclitaxel showing a sol-gel transition at 30° C. (Formulated according to Example 5). Paclitaxel incorporated as a cyclodextrin complex as 50% of total cyclodextrin added to the formulation. G' denotes storage modulus.
Figure 6:
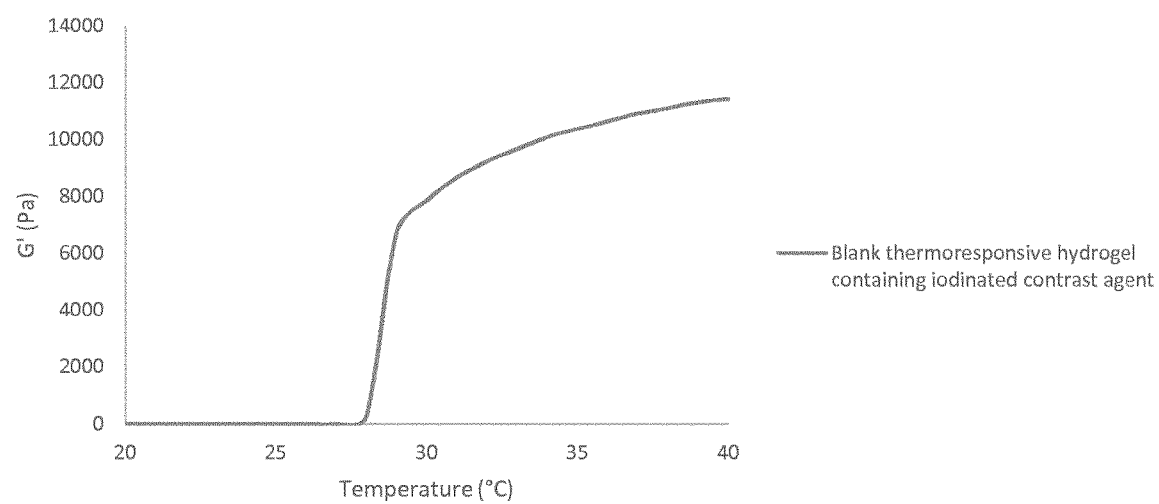
FIG. 6. Rheological temperature response curves (Example 10) obtained used an AR-1000 rheometer (TA Instruments) of thermo-responsive hydrogel containing iodinated contrast agent with sol-gel transition at 28° C. G' denotes storage modulus.
Figure 7:
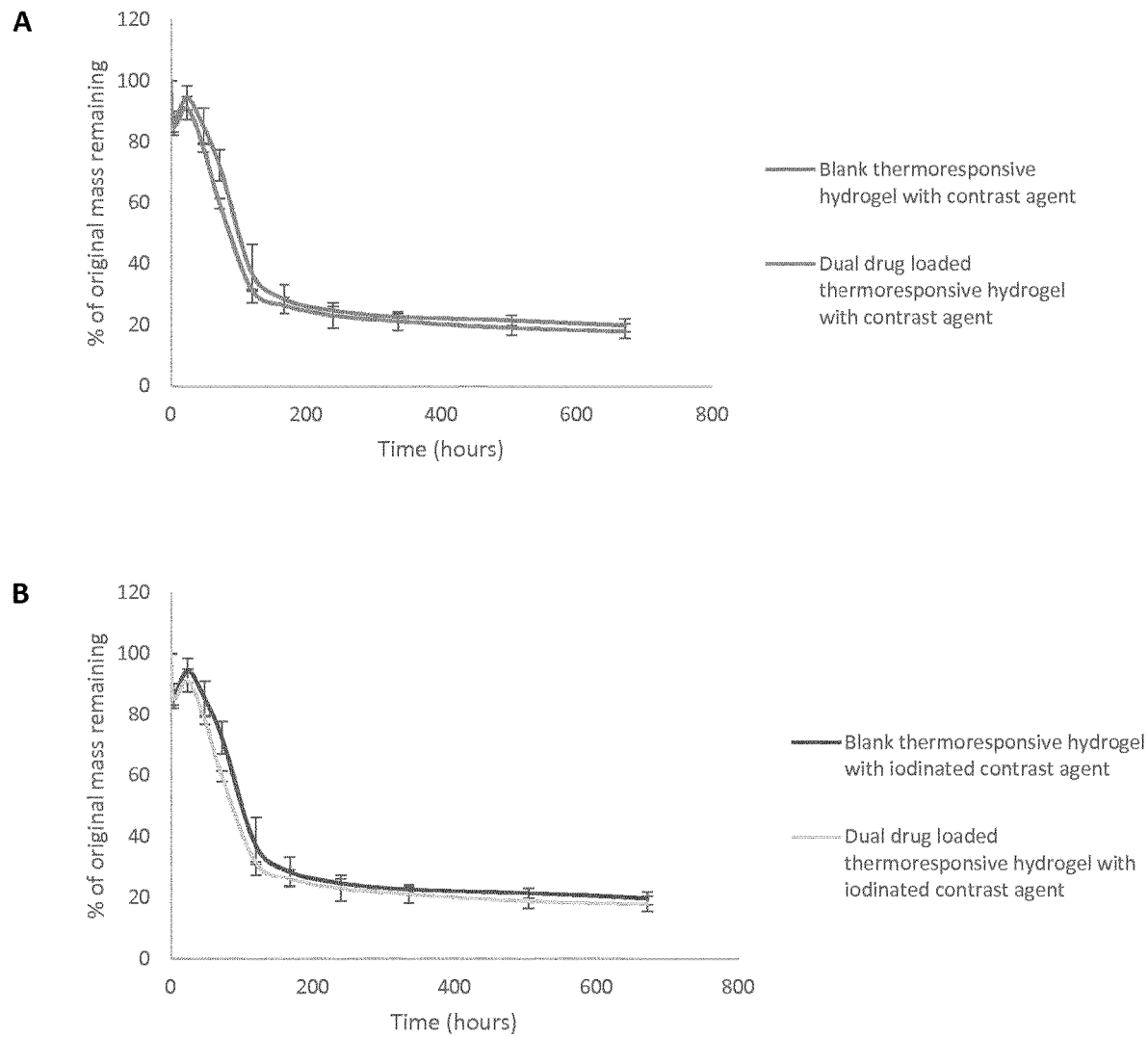
FIG. 7. In vitro disintegration (Example 11) (at 37° C.) of (A) blank thermo-responsive hydrogel and drug loaded thermo-responsive hydrogel with Paclitaxel and Cisplatin (formulated according to Example 1 and 4 respectively) and (B) blank thermo-responsive hydrogel and drug loaded thermo-responsive hydrogel with Paclitaxel and Cisplatin, containing iodinated contrast agent (formulated according to Example 6 and 7 respectively).
Figure 8:
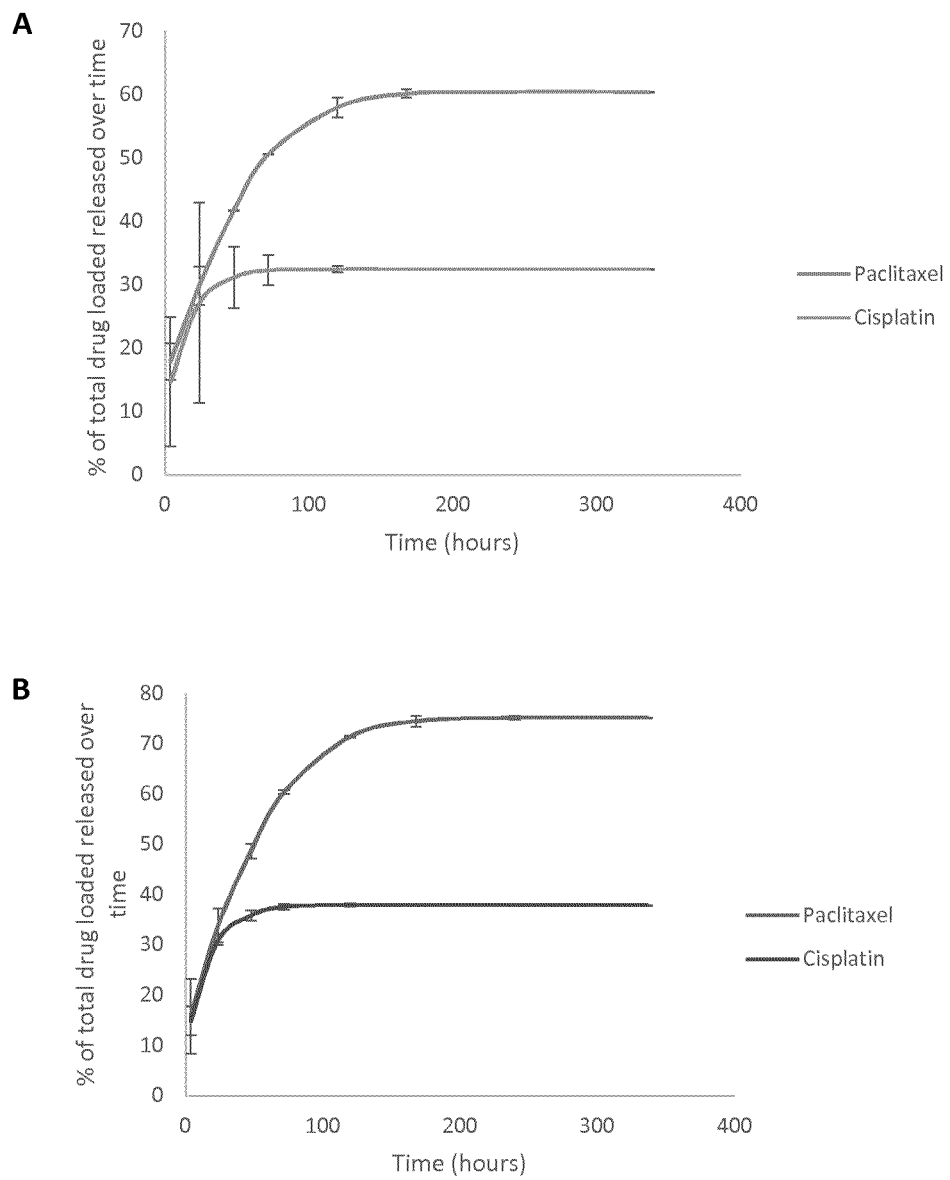
FIG. 8. In vitro release profile (at 37° C.) (Example 12) of Paclitaxel and Cisplatin from (A) drug loaded thermo-responsive hydrogel (formulated according to Example 4) and (B) drug loaded thermo-responsive hydrogel containing iodinated contrast agent (formulated according to Example 7)
Figure 9:
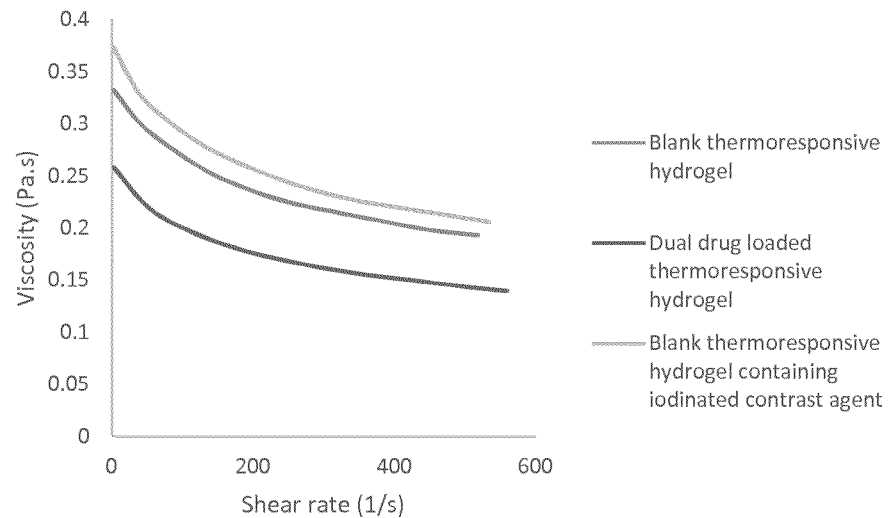
FIG. 9. Rheograms of steady state flow (Example 13) procedure on blank, drug loaded and iodinated contrast agent containing thermo-responsive hydrogel. Increasing shear stress lead to decreasing viscosity in all hydrogels indicating shear thinning behaviour of formulation.
Figure 10:
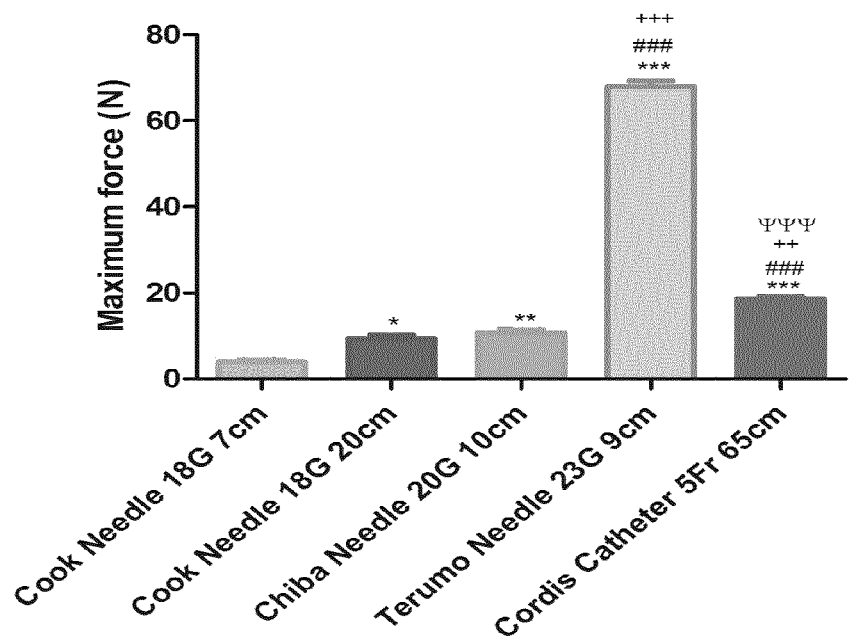
FIG. 10. Examples of injectability (Example 14) of blank thermo-responsive hydrogel containing iodinated contrast agent (formulated according to Example 5).
Figure 11:
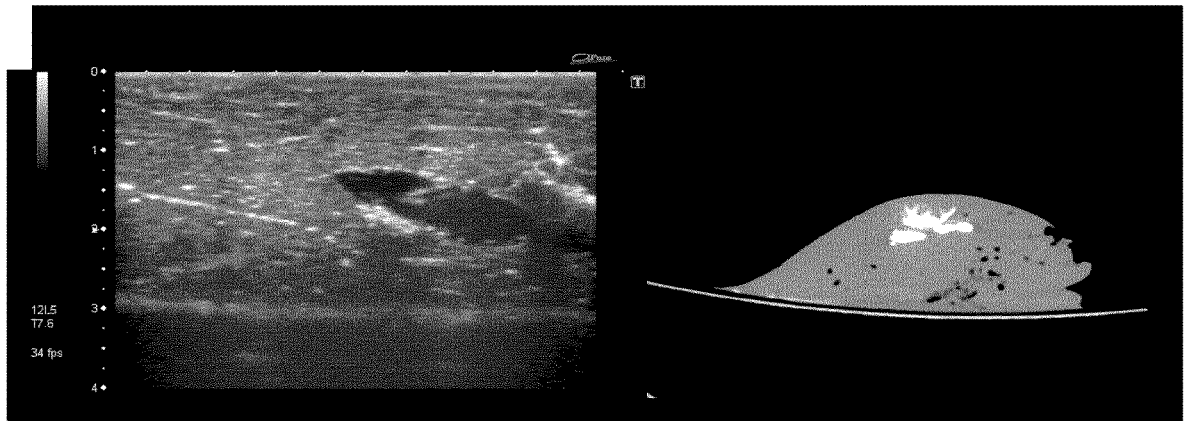
FIG. 11. Ultrasound (left) and CT (right) images (Example 15) of blank thermo-responsive hydrogel containing iodinated imaging agent (formulated according to Example 5).
Figure 12A:
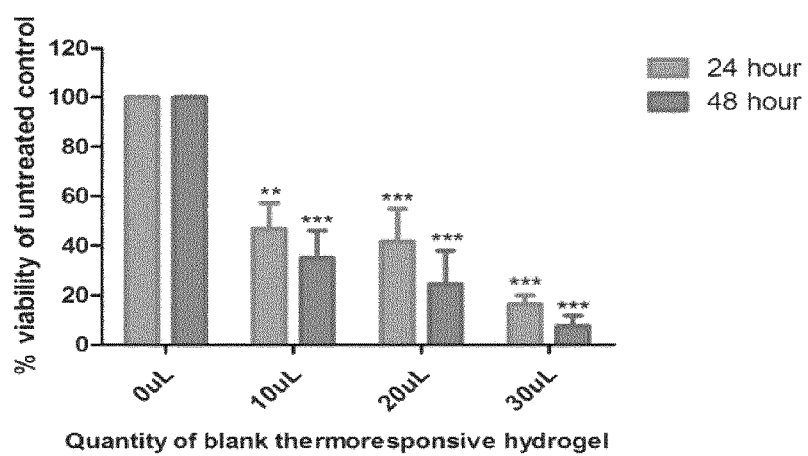
FIG. 12. Effect on viability (Example 16) of different doses of (A) blank and (B) drug loaded thermo-responsive hydrogel at 24 hours and 48 hours post treatment in a human non-small cell lung cancer cell lines, A549 cells. Data shown is represented as the mean+standard error of the mean (SEM) (n=3). (A)=$p<0.01$, *=$p<0.001$ compared to blank thermo-responsive hydrogel 0 uL at the same timepoint. (B)***=$p<0.001$ compared to Drug loaded thermo-responsive hydrogel 0 uL at the same timepoint. ##=$p<0.01$ compared to drug loaded thermo-responsive hydrogel 10 uL at the same timepoint.
Figure 12B:
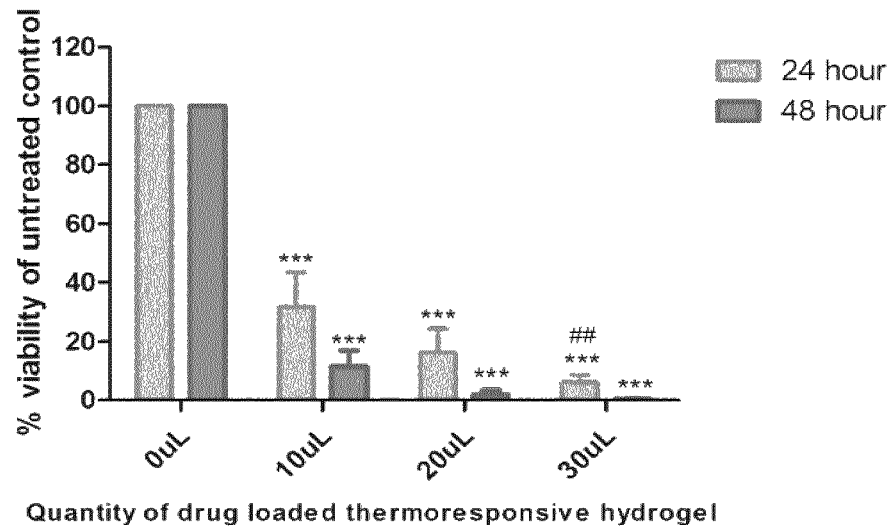
Figure 13A:
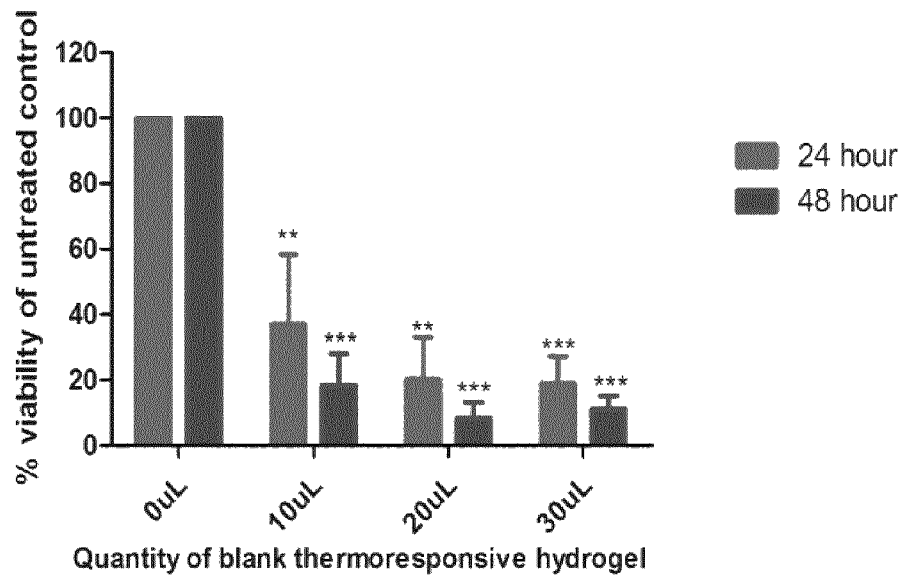
FIG. 13. Effect on viability of different doses of (A) blank and (B) drug loaded thermo-responsive hydrogel at 24 hours and 48 hours post treatment in a human pancreatic cancer cell line, Panc-1 cells. Data shown is represented as the mean+standard error of the mean (SEM) (n=2). (A)=$p<0.01$, *=$p<0.001$ compared to blank thermo-responsive hydrogel 0 uL at the same timepoint. (B)***=$p<0.001$ compared to Drug loaded thermo-responsive hydrogel 0 uL at the same timepoint. ##=$p<0.01$ compared to drug loaded thermo-responsive hydrogel 10 uL at the same timepoint.
Figure 13B:
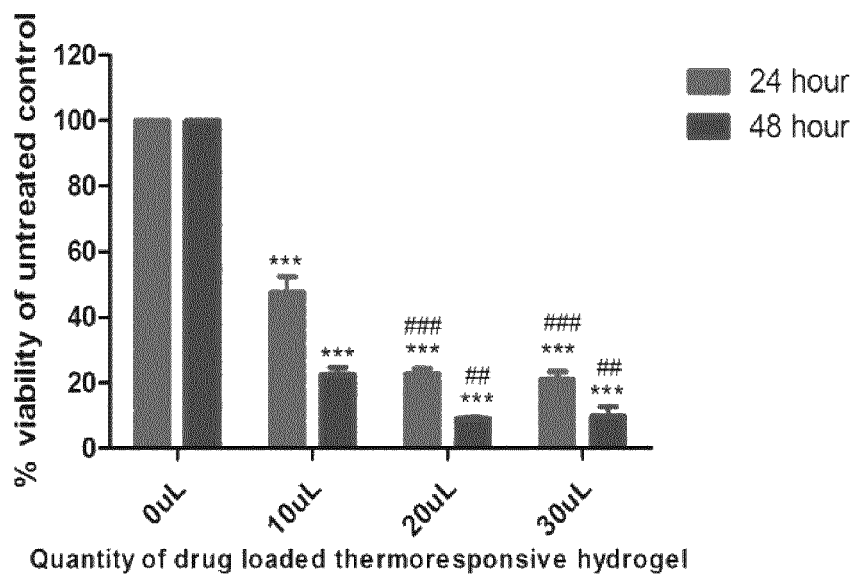

All publications, patents, patent applications and other references mentioned herein are hereby incorporated by reference in their entireties for all purposes as if each individual publication, patent or patent application were specifically and individually indicated to be incorporated by reference and the content thereof recited in full.

Definitions and General Preferences

Where used herein and unless specifically indicated otherwise, the following terms are intended to have the following meanings in addition to any broader (or narrower) meanings the terms might enjoy in the art:

Unless otherwise required by context, the use herein of the singular is to be read to include the plural and vice versa. The term "a" or "an" used in relation to an entity is to be read to refer to one or more of that entity. As such, the terms "a" (or "an"), "one or more," and "at least one" are used interchangeably herein.

As used herein, the term "comprise," or variations thereof such as "comprises" or "comprising," are to be read to indicate the inclusion of any recited integer (e.g. a feature, element, characteristic, property, method/process step or limitation) or group of integers (e.g. features, element, characteristics, properties, method/process steps or limitations) but not the exclusion of any other integer or group of integers. Thus, as used herein the term "comprising" is inclusive or open-ended and does not exclude additional, unrecited integers or method/process steps.

As used herein, the term "disease" is used to define any abnormal condition that impairs physiological function and is associated with specific symptoms. The term is used broadly to encompass any disorder, illness, abnormality, pathology, sickness, condition or syndrome in which physiological function is impaired irrespective of the nature of the aetiology (or indeed whether the aetiological basis for the disease is established). It therefore encompasses conditions arising from infection, trauma, injury, surgery, radiological ablation, poisoning or nutritional deficiencies.

As used herein, the term "proliferative disorder" refers to the group of diseases involving abnormal cell growth with the potential to spread to distant or local sites, especially means a malignant tumour. Typically, the cancer is selected from the group comprising: esophagogastric cancer; fibrosarcoma; myxosarcoma; liposarcoma; chondrosarcoma; osteogenic sarcoma; chordoma; angiosarcoma; endotheliosarcoma; lymphangiosarcoma; lymphangioendotheliosarcoma; synovioma; mesothelioma; Ewing's tumor; leiomyosarcoma; rhabdomyosarcoma; colon carcinoma; pancreatic cancer; breast cancer; ovarian cancer; prostate cancer; squamous cell carcinoma; basal cell carcinoma; adenocarcinoma; sweat gland carcinoma; sebaceous gland carcinoma; papillary carcinoma; papillary adenocarcinomas; cystadenocarcinoma; medullary carcinoma; bronchogenic carcinoma; renal cell carcinoma; hepatoma; bile duct carcinoma; choriocarcinoma; seminoma; embryonal carcinoma; Wilms' tumor; cervical cancer; uterine cancer; testicular tumor; lung carcinoma; small cell lung carcinoma; bladder carcinoma; epithelial carcinoma; glioma; astrocytoma; medulloblastoma; craniopharyngioma; ependymoma; pinealoma; hemangioblastoma; acoustic neuroma; oligodendroglioma; meningioma; melanoma; retinoblastoma; and leukemias.

As used herein, the term "solid tumour" refers to cancers of organs and tissue (as opposed to haematological malignancies), and ideally epithelial cancers. Examples of solid tumour cancers include pancreatic cancer, bladder cancer, prostate cancer, ovarian cancer, colorectal cancer (CRC), breast cancer, mesothelioma, renal cancer, lung cancer, hepatocellular cancer, cervical cancer, gastric cancer, esophageal cancer, head and neck cancer, melanoma, neuroendocrine cancer. Suitably, the solid tumour cancer suitable for treatment and prognosis according to the methods of the invention can be selected from the list above.

As used herein, the term "treatment" or "treating" refers to an intervention (e.g. the administration of an agent to a subject) which cures, ameliorates or lessens the symptoms of a disease or removes (or lessens the impact of) its cause(s) (for example, the reduction in accumulation of pathological levels of lysosomal enzymes). In this case, the term is used synonymously with the term "therapy". In one embodiment, the therapy of the invention is an adjunct therapy. In one embodiment, the therapy of the invention comprises administering a hydrogel of the invention, in combination with another forms of therapy.

Additionally, the terms "treatment" or "treating" refers to an intervention (e.g. the administration of an agent to a subject) which prevents or delays the onset or progression of a disease or reduces (or eradicates) its incidence within a treated population. In this case, the term treatment is used synonymously with the term "prophylaxis".

As used herein, the term "intratumourally" refers to administration directly into a tumour by injection, or delivery to an existing cavity in the body or a cavityformed as a result of surgical resection of all or part of a solid tumour. Intratumoral administration generally involves injection using a suitable syringe.

In the context of treatment and effective amounts as defined above, the term subject (which is to be read to include "individual", "animal", "patient" or "mammal" where context permits) defines any subject, particularly a mammalian subject, for whom treatment is indicated. Mammalian subjects include, but are not limited to, humans, domestic animals, farm animals, zoo animals, sport animals, pet animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; and rodents such as mice, rats, hamsters and guinea pigs. In preferred embodiments, the subject is a human.

As used herein, the term "thermo-responsive" as applied to a hydrogel means a polymer based material which forms a solution/colloidal dispersion at room temperature which subsequently transitions to a semi-solid hydrogel at an elevated temperature within a defined range. The hydrogel is typically sufficiently fluid at room temperature (for example 18-23° C.) to allow the hydrogel be injected into the body using a convention syringe, but at least partially solidifies at body temperature (for example 24-37° C.) to form a solid or semi-solid that is more easily retained at a site in the body.

As used herein, the term "thermo-responsive base hydrogel" refers to a polymer capable of forming a hydrogel that exhibits thermo-responsive properties. Examples include poloxamers, hydroxypropylcellulose, Poly(N-isopropylacrylamide) (PNIPAAm) and triblock copolymer PLGA-PEG-PLGA (ReGel®). The base thermo-responsive polymer solution forms the matrix of the hydrogel, in which the crosslinked interpenetrating network is formed, and in which the payload (when employed) is distributed. The payload is generally some form of active agent, for example a chemotherapeutic drug (which may be provided as an inclusion complex with an inclusion complexer such as a HP cyclodextrin), or it may be another form of active agent such as a protein, peptide, sugar, nucleic acid, antibody, antibody fragment, cell, or growth factor. The cell may be a stem cell. The cell may be genetically modified. In some embodiment, the hydrogel does not include a payload. In some embodiments, the hydrogel of the invention comprises 15-25% base hydrogel (i.e. poloxamer). In one embodiment, the hydrogel comprises less than 20% base hydrogel, for example, less than 19 or 18% base hydrogel. In one embodiment, the hydrogel of the invention comprises 15-20%, 15-19%, 16-18%, or about 17% of the base hydrogel.

As used herein, the term "uncured" as applied to the hydrogel of the invention means that the hydrogel has not been treated with heat or other means to harden the hydrogel in a curing process. This means that the hydrogel typically has a representative viscosity at 20° C. of 0.7 to 0.05, 0.7 to 0.1 or 0.5 to 0.05 Pa·s$^{-1}$.

As used herein, the term "injectable" as applied to a thermo-responsive hydrogel means that the hydrogel at ambient temperature is sufficiently fluid to allow it be injected intratumorally in a subject. Representative viscosity for an injectable hydrogel at 20° C. are 0.5-0.05 Pa·s, shear stress dependant as measured using flow rheometry (viscosity) measurements on a stress controlled rheometer (TA instruments).

As used herein, the term "poloxamer" refers to nonionic triblock copolymers having a central hydrophobic chain and two flanking hydrophilic chains arranged in a A-B-A triblock structure. They are described in U.S. Pat. No. 3,740,421. Poloxamer 407 is a type of poloxamer having a central polypropylene glycol block flanked by two polyethylene glycol blocks. It is sold by BASF under the trade name PLURONIC F127 and by Croda under the trade name SYNPERONIC PE/F127. Poloxamer 188 could also be used in conjunction with Poloxamer 407.

As used herein the term "hydrogel strengthening agent" refers to a polymer capable of being crosslinked with genipin and forming an interpenetrating scaffold within the thermos-responsive hydrogel. Examples include methyl cellulose, dextan, carrageenan, chitosan, and pluronic R.

As used herein, the term "chitosan" refers to the natural polysaccharide derived from the shells of crustaceans such as crabs and shrimp. The chitosan may be provided as a salt, for example a chloride salt of chitosan. The term also includes chitosan derivatives, especially water-soluble chitosan derivatives. In one embodiment, the chitosan has a degree of deacetylation of up to 90%. In one embodiment, the chitosan has molecular weight of 150 to 400 KDa. In one embodiment, the thermo-responsive hydrogel comprises 0.1-5.0% gel strengthening agent (i.e. chitosan) (w/w). In one embodiment, the thermo-responsive hydrogel comprises 0.1-1.0% gel strengthening agent (i.e. chitosan) (w/w). In one embodiment, the thermo-responsive hydrogel comprises 0.3-0.5% gel strengthening agent (i.e. chitosan) (w/w).

As used herein, the term "genipin" refers to an aglycone derived from irdoid glycoside called geniposide, which is present in fruit of Gardeniajasminoides. Typically, the hydrogel of the invention comprises 0.01-2.0% genipin (w/w). Typically, the hydrogel of the invention comprises 0.05-1.0% genipin (w/w). In one embodiment, the thermo-responsive hydrogel comprises 0.1-0.5% genipin (w/w). In one embodiment, the thermo-responsive hydrogel comprises 0.05-0.20%, or 0.05-0.15% genipin (w/w). In one embodiment, the thermo-responsive hydrogel comprises about 0.1% genipin (w/w).

As used herein, the term "inclusion complexer" refers to a compound having a cavity capable of receiving a guest compound. Examples include cyclodextrins, especially beta-cyclodextrins (for example 2-Hydroxypropyl β-cyclodextrin and methyl beta cyclodextrin. Typically, the hydrogel of the invention comprises 1-20% inclusion complexer. Typically, the hydrogel of the invention comprises 5-20% inclusion complexer. Typically, the hydrogel of the invention comprises 8-15% inclusion complexer.

"2-Hydroxypropyl β-cyclodextrin" or "HP-β-CD" is a form of cyclodextrin that functions as an effective inclusion copmplexer. It is described in Bonacucina et al (Bonacucina G, Spina M, Misici-Falzi M, Cespi M, Pucciarelli S, Angeletti M, et al. Effect of hydroxypropyl beta-cyclodextrin on the self-assembling and thermogelation properties of Poloxamer 407. Eur J Pharm Sci. 2007; 32:115-22.). Typically, the hydrogel of the invention comprises 1-20% Hydroxypropyl β-cyclodextrin. Typically, the hydrogel of the invention comprises 5-20% Hydroxypropyl β-cyclodextrin. Typically, the hydrogel of the invention comprises 8-15% Hydroxypropyl β-cyclodextrin.

As used herein, the term "active agent" should be understood to mean biological and non-biological agents that are therapeutically active in mammals, such as drugs, cells (eukaryotic and prokaryotic) and biological molecules such as protein, peptides, and nucleic acids, and conjugates of drugs and biological molecules such as antibody drug conjugates. In one embodiment, the biologically active agent is a nucleic acid selected from DNA, RNA, mRNA, tRNA, shRNA, siRNA, gRNA. In one embodiment, the biologically active agent is a therapeutic factor selected from antiangioenicantibodies, antibody fragments, cytokines, interleukins, interferons, biopharmaceutical products, proteins, nucleic acids. In one embodiment, the therapeutically active agent is a pharmaceutical, for example a chemotherapeutic agent. Typically, the hydrogel of the invention comprises 0.01 to 10% active agent (w/w). In one embodiment, the thermo-responsive hydrogel comprises 0.1 to 5% active agent (w/w). In one embodiment, the thermo-responsive hydrogel comprises 0.1 to 1.0% active agent (w/w). In one embodiment, the thermo-responsive hydrogel comprises 1.0 to 5.0% active agent (w/w).

As used herein, the term "chemotherapeutic agent" refers to an agent that kills cancer cells optionally by inducing cancerous cells to commit to cell death. Suitable chemotherapeutic agents will be known to those skilled in the art. Such chemotherapeutic agents include but are not limited to; monoclonal antibodies including VEGF inhibitors, EGFR inhibitors, T-cell activators, PD-1 inhibitors, EGFR(HER2) inhibitors, VEGFR2 inhibitors, and IL-6 inhibitors, Alkylating agents, Anthracyclines, Antimetabolites, Cytotoxic Antibiotics, Plant Alkaloids, Platinum Compounds, Podophyllotoxin derivatives, Topoisomerase I inhibitors, *Vinca* Alkaloids, Interluekins, Thalidomide (and related analogues), Protein Kinase inhibitors, Metformin, and antineovascularisation drugs. Examples of chemotherapeutic agent are provided in Table 1 below). In one embodiment, the chemotherapeutic agent is selected from cisplatin, paclitaxel, gemcitabine, or a combination thereof such as a combination of cisplatin and paclitaxel, or a combination of gemcitabine and paclitaxel.

TABLE 1

| Class | Group | Drugs |
|---|---|---|
| Monoclonal Antibodies | VEGF inhibitors | Bevacizumab |
| | EGFR inhibitors | Cetuximab |
| | | Panitumumab |
| | T-cell activation | Ipilimumab |
| | PD-1 inhibitors | Nivolumab |
| | | Pembrolizumab |
| | EGFR2 (HER2) inhibitor | Pertuzumab |
| | | Trastuzumab |
| | VEGFR-2 inhibitor | Ramucirumab |
| | IL-6 inhibition | Siltuximab |
| Cytotoxic drugs | Alkylating Agents | Carmustine |
| | | Cyclophosphamide |
| | | Dacarbazine |
| | | Estramustine |
| | | Ifosfamide |
| | | Lomustine |
| | | Temozolomide |
| | | Treosulfan |
| | Anthracyclines | Doxorubicin HCl |
| | | Epirubicin HCl |
| | | Idarubicin HCl |
| | | Mitoxantrone |
| | Antimetabolites | Capecatibine |
| | | Flourouracil |
| | | Gemcitabine |
| | | Methotrexate |
| | | Pemetrexed |
| | Cytotoxic Antibiotics and Related substances | Bleomycin |
| | | Mitomycin |
| | Plant Alkaloids | Trabectedin |
| | Platinum Compounds | Carboplatin |
| | | Cisplatin |
| | | Oxaliplatin |
| | Podophyllotoxin derivatives | Etopside |
| | | Docetexel |
| | | Paclitaxel |
| | Topoisomerase I inhibitors | Irinotecan HCl |
| | | Topotecan |
| | Vinca Alkaloids | Vinblastine sulfate |
| | | Vincristine sulfate |
| | | Vinflunine |
| | | Vinorelbine |
| | Thymidylate synthase inhibition | Raltitrexed |

TABLE 1-continued

| Class | Group | Drugs |
|---|---|---|
| Immunostimulants | Interleukins | Aldesleukin |
| Immunosuppressants | Thalidomide and related analogues | Lenalidomide |
| | | Pomalidomide |
| | | Thalidomide |
| Antineoplastic drugs | Protein Kinase Inhibitors | Afatinib |
| | | Axitinib |
| | | Cabozantinib |
| | | Ceritinib |
| | | Crizotinib |
| | | Erlotinib |
| | | Everolimus |
| | | Gefitinib |
| | | Lapatinib |
| | | Pazopanib |
| | | Regorafenib |
| | | Sorafenib |
| | | Sunitinib |
| | | Temsirolimus |
| | | Vandetanib |
| Antineovascularisation drugs | VEGF inhibitor | Aflibercept |

As used herein, an effective amount or atherapeutically effective amount of an agent defines an amount that can be administered to a subject without excessive toxicity, irritation, allergic response, or other problem or complication, commensurate with a reasonable benefit/risk ratio, but one that is sufficient to provide the desired effect, e.g. the treatment or prophylaxis manifested by a permanent or temporary improvement in the subject's condition. The amount will vary from subject to subject, depending on the age and general condition of the individual, mode of administration and other factors. Thus, while it is not possible to specify an exact effective amount, those skilled in the art will be able to determine an appropriate "effective" amount in any individual case using routine experimentation and background general knowledge. A therapeutic result in this context includes eradication or lessening of symptoms, reduced pain or discomfort, prolonged survival, improved mobility and other markers of clinical improvement. The amount of drug per intratumoral administration will be determined based on tumour size, in combination with imaging to ensure adequate coverage of the tumour. For example, in ethanol ablation therapies ethanol volume for delivery is based on tumour size;

Vol ethanol $(ml) = 4/3\pi[(D/2+0.5)]^3$ where D=tumour dimension (Kuang et al., 2011)

Vol ethanol $(ml) = 4/3 \times \pi(Y+1)^3$ where Y=radius of tumour (Lin et al., 2005)

The hydrogel could be administered on repeated occasions at defined intervals dependent on clinical response and toxicity.

Typically, the hydrogel of the invention comprises 0.01 to 10% chemotherapeutic agent (w/w). In one embodiment, the thermo-responsive hydrogel comprises 0.1 to 5% chemotherapeutic agent (w/w). In one embodiment, the thermo-responsive hydrogel comprises 0.1 to 1.0% chemotherapeutic agent (w/w). In one embodiment, the thermo-responsive hydrogel comprises 1.0 to 5.0% chemotherapeutic agent (w/w).

As used herein, the term "poorly soluble" as applied to a chemotherapeutic agent means an agent for which at least 30 mls of water is need to dissolve 1 g of the agent.

As used herein, the term "cells" should be understood to mean any type of eukaryotic or prokaryotic cell, including for example, pancreatic cells, pancreatic Islets, smooth muscle cells, epithelial cells, endothelial cells, progenitor cells, mesenchymal stem cells, antibody producing cells, stem cells, adult stem cells or human or non-human origin, or bacterial cells. The cells may be wild-type cells, or they may be cells that are genetically engineered. The cells may be obtained from the patient undergoing therapy (autologous cell implantation) or they may be obtained from a different person (allogenic cell implantation) or another species (xenogenic cell implantation). Generally, the cells are living cells. Cells may be obtained from tissue of the patient or donors or from cell depositories or research Institutions.

As used herein, the term "contrast agent" refers to an agent used to enhance the visibility of the thermo-responsive hydrogel of the invention in the body using for example X-ray based imaging techniques such as radiography, fluoroscopy, and CT scanning and ultrasound. They are also known as radiocontrast agents. Generally the contrast dye is an iodinated contrast agent. Examples include distrizoate, metrizoate, iothalamate, ioxaglate, iopamidol, iohexol, ioxilan, iopromide, iodixanol, ioversol. Typically, the hydrogel of the invention comprises 1-10%, 2-9% and typically 2-7% contrast agent (w/w).

As used herein, the term "aqueous base" means water, typically distilled water or an aqueous solvent or buffer. In one embodiment, the aqueous base has a pH of 5-7, typically about 6.

Exemplification

The invention will now be described with reference to specific Examples. These are merely exemplary and for illustrative purposes only: they are not intended to be limiting in any way to the scope of the monopoly claimed or to the invention described. These examples constitute the best mode currently contemplated for practicing the invention.
Materials
Poloxamer 407 (P407)
Chitosan Chloride salt (CS)
2-Hydroxypropyl-β-Cyclodextrin (2HPβCD)
Genipin (GP)
Cisplatin
Paclitaxel
Gemcitabine
Iodinated contrast agent (Iodixonal)

Example 1—Blank Thermo-Responsive Hydrogels (Non-Drug Loaded). Comparison of Hydrogel of the Invention with Jordan Hydrogels 2-Hydroxypropyl-β-Cyclodextrin (HP-β-CD) (10% w/w) was dissolved in $dH_2O$ at pH<6 and stirred at room temperature, for a minimum of thirty minutes until fully dissolved. The solution was then chilled on ice until at 4° C. Chitosan chloride salt (CS) (0.5% w/w) was added to the solution with stirring, and maintained at 4° C. Poloxamer 407 (P407) (17%-20% w/w) was then sprinkled into the HP-β-CD/CS solution with continuous stirring and allowed to stir for a minimum of 1 hour until all components were fully in solution. This solution was then stored at 4° C. to ensure full hydration of the polymer solution (normal minimum period 8-12 hrs). Genipin (GP) (0.1%-0.3% w/w) was then added to the solution and allowed to stir for a minimum of 4 hours on ice to ensure complete dissolution. The solution was weighed and made up to final weight with $dH_2O$. Gels GF 1 and 2 were placed in glass vials and left to cure in a water bath for 24 hours at 37° C. This process is outlined in the schematic shown in FIG. 1. Gel GF1 is the hydrogel of Jordan. The thermoresponsivity and storage modulus (G') are provided for all hydrogels in Table 2 below.

TABLE 2

|  | Gel Formulation | | | | |
| --- | --- | --- | --- | --- | --- |
|  | 1 | 2 | 3 | 4 | 5 |
| P407 (% w/w) | 20 | 20 | 20 | 17 | 17 |
| HP-β-CD (% w/w) | 10 | 10 | 10 | 10 | 10 |
| CS (% w/w) | 0.5 | 0.5 | 0.5 | 0.5 | 0.5 |
| GP (% w/w) | 0.3 | 0.3 | 0.1 | 0.3 | 0.1 |
| TPP (% w/w) | — | 0.2 | — | — | — |
| 24 hour curing period | ✓ | ✓ | — | — | — |
| Thermoresponse (° C.) | 25 | 24 | 30 | 33 | 29 |
| G' @ 37° C. (Pa) | 13,210 | 21,580 | 7,428 | 7,679 | 11,380 |

The sol-gel transition temperature is determined according to Example 10.

Example 2—Complexation of Paclitaxel with 2-Hydroxypropyl-β-Cyclodextrin

The required amount of HPCD was dissolved in the required amount of $dH_2O$ on a stirring plate for five minutes at room temperature. The required amount of Paclitaxel was then added to this stirring solution. The solution was stirred at high speed for thirty minutes. The speed was reduced and the solution was allowed to stir for 72 hours to ensure complete dissolution. The solution was frozen at −80° C. The frozen solution was freeze dried overnight using a Labcono Freeze Dryer and vacuum pump to produce a lyophilised powder consisting of Pac-HPCD inclusion complexes.

Example 3—Thermo-Responsive Hydrogel Drug Loaded with Cisplatin and Paclitaxel (with HPβCD Added as Paclitaxel Complex The polymer solution loaded with Cisplatin and Paclitaxel was prepared with modifications to Example 1. Cisplatin was dissolved in the required amount of $dH_2O$. The Paclitaxel-HPICD (containing HPICD 10% w/w of final formulation) complex (prepared as per Example 2) was dissolved in the Cisplatin solution at pH<6 and stirred at room temperature, for thirty minutes. The solution was then chilled until at 4° C. CS (0.5% w/w) was added to the solution with stirring, and maintained at 4° C. P407 (17% w/w) was then sprinkled into the HP-β-CD/CS solution with continuous stirring and allowed to stir for a minimum of 1 hour until all components were fully in solution. This solution was then stored at 4° C. to ensure full hydration of the polymer solution (normal minimum period 8-12 hrs). GP (0.1% w/w) was then added to the solution and allowed to stir for a minimum of 4 hours on ice to ensure complete dissolution. The solution was weighed and made up to final weight with $dH_2O$.

Example 4—Dual Drug Loaded Thermo-Responsive Hydrogel with Cisplatin and Paclitaxel (with Final HPβCD Concentration Split Between paclitaxel Complex and 'Free' HPβCD)

The final concentration of HPβCD to be contained in the formulation was split between the Paclitaxel complex and uncomplexed 2-Hβ-CD at a ratio of 1:2. Cisplatin was dissolved in the required amount of $dH_2O$. The Paclitaxel complex (made as per Example 2) and the required amount of free HPCD powder to bring the final amount of HPCD to 10% w/w was dissolved in the Cisplatin solution at pH<6 and stirred at room temperature, for thirty minutes. The solution was then chilled on ice until at 4° C. CS (0.5% w/w) was added to the solution with stirring, and maintained at 4° C. P407 (17% w/w) was then sprinkled into the HP-β-CD/CS solution with continuous stirring and allowed to stir for a minimum of 1 hour until all components were fully in solution. This solution was then stored at 4° C. to ensure full hydration of the polymer solution (normal minimum period 8-12 hrs). GP (0.1% w/w) was then added to the solution and allowed to stir for a minimum of 4 hours on ice to ensure complete dissolution. The solution was weighed and made up to final weight with $dH_2O$. This process is outlined in the schematic shown in FIG. 1.

Example 5—Dual Drug Loaded Thermo-Responsive Hydrogel with Gemcitabine and Paclitaxel (with Final HPβCD Concentration Split Between Paclitaxel Complex and 'Free' HPβCD)

The final concentration of HPCD to be contained in the formulation was split between the Paclitaxel complex and uncomplexed 2-Hβ-CD at a ratio of 1:1. Gemcitabine was dissolved in the required amount of $dH_2O$. The Paclitaxel complex (made as per Example 2) and the required amount of free HPCD powder to bring the final amount of HPCD to 10% w/w was dissolved in the Cisplatin solution at pH<6 and stirred at room temperature, for thirty minutes. The solution was then chilled on ice until at 4° C. CS (0.5% w/w) was added to the solution with stirring, and maintained at 4° C. P407 (17% w/w) was then sprinkled into the HP-β-CD/CS solution with continuous stirring and allowed to stir for a minimum of 1 hour until all components were fully in solution. This solution was then stored at 4° C. to ensure full hydration of the polymer solution (normal minimum period 8-12 hrs). GP (0.1% w/w) was then added to the solution and allowed to stir for a minimum of 4 hours on ice to ensure complete dissolution. The solution was weighed and made up to final weight with $dH_2O$.

Example 6—Blank Thermo-Responsive Hydrogel Containing Iodinated Contrast Agent

HPβCD (10% w/w) was dissolved in the required amount of $dH_2O$ containing the iodinated imaging agent (Iodixonal 2-7% w/w) and stirred at room temperature, for thirty minutes. The solution was then chilled on ice until at 4° C. CS (0.5% w/w) was added to the solution with stirring, and maintained at 4° C. P407 (17% w/w) was then sprinkled into the HP-β-CD/CS solution with continuous stirring and allowed to stir for a minimum of 1 hour until all components were fully in solution. This solution was then stored at 4° C. to ensure full hydration of the polymer solution (normal minimum period 8-12 hrs). GP (0.1% w/w) was then added to the solution and allowed to stir for a minimum of 4 hours on ice to ensure complete dissolution. The solution was weighed and made up to final weight with $dH_2O$.

Example 7—Dual Drug Loaded Thermo-Responsive Hydrogel with Cisplatin and Paclitaxel (with Final HPβCD Concentration Split Between Paclitaxel Complex and 'Free' HPβCD) Containing Iodinated Contrast Agent The final concentration of HPCD to be contained in the formulation was split between the Paclitaxel complex and uncomplexed HPβCD at a ratio of 1:2. Cisplatin was dissolved in the required amount of $dH_2O$ containing the iodinated contrast agent (Iodixonal 2-7% w/w). The Paclitaxel complex (made as per Example 2) and the required amount of free HPCD powder to bring the final amount of HPCD to 10% w/w was dissolved in the Cisplatin solution at pH<6 and stirred at room temperature, for thirty minutes. The solution was then chilled on ice until at 4° C. CS (0.5% w/w) was added to the solution with stirring, and maintained at 4° C. P407 (17% w/w) was then sprinkled into the HP-β-CD/CS solution with continuous stirring and allowed to stir for a minimum of 1 hour until all components were fully in solution. This solution was then stored at 4° C. to ensure full hydration of the polymer solution (normal minimum period 8-12 hrs). GP (0.1% w/w) was then added to the solution and allowed to stir for a minimum of 4 hours on ice to ensure complete dissolution. The solution was weighed and made up to final weight with $dH_2O$.

Example 8—Freeze-Drying of Blank Thermo-Responsive Hydrogel (without or with Iodinated Contrast Agent)

Blank thermo-responsive hydrogels without or with iodinated contrast agent were prepared as outlined in Examples 1 or 6 respectively. A known weight of the polymer solution was transferred to a suitable beaker and flash frozen using liquid nitrogen. The frozen solution was then freeze-dried under vacuum at −55° C. for 48 hours to produce a lyophilised powder. The powder was then rehydrated and brought up to original weight with $dH_2O$, stirred for a minimum of 6 hours and allowed to rehydrate at 4° C. overnight.

Example 9—Freeze-Drying of Dual Drug Loaded Thermo-Responsive Hydrogel with

Cisplatin and Paclitaxel (drug loaded with or without iodinated contrast agent) Dual drug loaded thermo-responsive hydrogels were prepared unlabelled or labelled with iodinated contrast agent as per Examples 4 or 7 respectively, with modifications. The hydrogels were prepared without the addition of Cisplatin. The Paclitaxel alone loaded polymer solution was transferred to a suitable beaker and flash frozen using liquid nitrogen. The frozen solution was then freeze-dried under vacuum at −55° C. for 48 hours to produce a lyophilised powder. The powder was then rehydrated and brought up to original weight with $dH_2O$ containing the required amount of Cisplatin for the final formulation, stirred for a minimum of 6 hours and allowed to rehydrate at 4° C. overnight.

Example 10—Determination of Sol-Gel Transition Temperature

The thermo-responsiveness of the various hydrogel formulations were assessed rheologically using oscillatory measurements, performed on an AR-1000 constant stress rheometer (TA instruments) with built-in temperature and gap calibration. The rheometer was equipped with cone/plate geometry (40 mm diameter, 4° cone angle). Degassed samples were dispensed onto the temperature controlled rheometer plate, pre-equilibrated to 20° C. A solvent trap, containing water, was used to cover the sample to prevent evaporation from the sample during the rheological testing. A water-bath (LAUDA-Ecoline) controlled the temperature of the peltier plate during testing. The temperature of the sample plate was controlled within +/−0.1° C. of the desired value at all times during testing. Prior to testing the geometery gap was calibrated. Following loading of excess sample, the geometry was lowered to this pre-determined gap. Excess hydrogel was removed with a spatula and discarded to ensure correct filling was achieved. Samples were allowed to equilibrate for a pre-determined time before commencing testing. Data was processed using TA Data Analysis software. All samples were analysed in triplicate.

Temperature sweeps from 20° C.-40° C. were carried out on all hydrogel formulations. The sol-gel transition temperature was defined as the temperature at which gelation had occurred. The gelation point is defined as the temperature at which the storage modulus (G') is equal to the loss modulus (G"). Therefore, gelation was deemed to have occurred when G'>G". Appropriate sol-gel transition temperature was deemed to be a temperature above average room temperature (21° C.) and ideally close to body temperature (37° C.). The temperature was increased at a rate of 1° C./minute, with oscillatory stress and angular frequency remaining constant.

Example 11—In-Vitro Disintegration Assay

A defined amount of the polymer solution (1 g) was weighed out into glass vials, and the total weight of the solution and vial was recorded. The polymer solution was allowed to gel for thirty minutes at 37° C. to ensure complete gelation had taken place. 1 ml of pre-warmed Phosphate Buffered Saline (PBS) (pH7.4) was added to the hydrogel. At pre-determined timepoints 1 ml of PBS was completely removed from the glass vial and the weight of the hydrogel and glass vial was recorded. The hydrogel was then returned to the waterbath and 1 ml of fresh pre-warmed PBS was added to the falcon tube. This process was repeated at pre-determined timepoints for 28 days. All experiments were conducted in triplicate and repeated as three individual experiments.

Example 12—In-Vitro Release Profile Assay

A defined amount of the polymer solution (1 g) was weighed out into glass vials. The polymer solution was allowed to gel for thirty minutes at 37° C. to ensure complete gelation had taken place. 1 ml of pre-warmed Phosphate Buffered Saline (PBS) (pH7.4) was added to the hydrogel. At pre-determined timepoints 1 ml of PBS was completely removed from the glass vial and stored at −20° C. until analysis. The hydrogel was then returned to the waterbath and 1 ml of fresh pre-warmed PBS was added to the falcon tube. This process was repeated at pre-determined timepoints for 28 days. All experiments were conducted in triplicate and repeated as three individual experiments.

ICP-MS was carried out for the detection of Cisplatin. Calibration curves were produced using platinum (Pt) standards (1000 mg/L Pt in Hydrochloric acid), diluted to appropriate parts per million (ppm) using PBS. Samples were manually introduced into the ICP-MS. The following parameters were used in analysis: power 1.2 kW, plasma flow 15 L/min, auxiliary flow 1.5 L/min, nebuliser pressure 200 kPa. The analyte detection wavelength was set for Pt at 214.423 nm. All samples were analysed in triplicate.

HPLC was conducted on an Agilent Technologies 1120 Compact L.C with a UV detector. Paclitaxel HPLC was developed based on a method published by Cho et al. (2004). HPLC was carried out on a Synergi 4u Hydro-RP 80A New Column (150×4.6 mm) (Phenomenex, Cheshire, UK). Column temperature was uncontrolled. The mobile phase consisted of acetonitrile:$H_2O$ (55:45). The flow rate was 1 ml/min, with a total run time of 10 minutes. UV detection of Paclitaxel was carried out at 227 nm. All samples were analysed in a minimum of duplicate.

Example 13—Flow Rheology (Viscosity) Measurements

Viscosity testing of the various hydrogel formulations were assessed using flow rheology, performed on an AR-1000 constant stress rheometer (TA instruments) with built-in temperature and gap calibration. The rheometer was equipped with cone/plate geometry (40 mm diameter, 4° cone angle). Degassed samples were dispensed onto the temperature controlled rheometer plate, pre-equilibrated to 20° C. A solvent trap, containing water, was used to cover the sample to prevent evaporation from the sample during the rheological testing. A water-bath (LAUDA-Ecoline) controlled the temperature of the peltier plate during testing. The temperature of the sample plate was controlled within +/−0.1° C. of the desired value at all times during testing. Prior to testing the geometery gap was calibrated. Following loading of excess sample, the geometry was lowered to this pre-determined gap. Excess hydrogel was removed with a spatula and discarded to ensure correct filling was achieved. Samples were allowed to equilibrate for a pre-determined time before commencing testing. Data was processed using TA Data Analysis software. All samples were analysed in triplicate.

Steady state flow experiments were carried out at 20° C. to determine how the hydrogel will behave under increasing shear stress. The viscosity of the sample is determined over a range of shear stresses from 1 Pa to 100 Pa.

Example 14—Injectability Assay

Uniaxial tensile testing was carried out to determine the force required to expel gel from a syringe fitted with a needle or catheter, as specified in Table 3, using a mechanical testing machine (Z050, Zwick/Roell, Germany), fitted with a 5 kN load cell. Hydrogel samples were loaded into 2 ml leur-lock syringes (BD, Dublin, Ireland) and kept chilled on ice before tensile testing to ensure that the samples remained in liquid state. The appropriate medical device was attached to the syringe via luer-lock to determine the maximum force required to expel a defined volume of the hydrogel.

Fixed grips were mounted onto the tensile testing machine for all tests, and the syringe was clamped into position attached to the load cell. A pre-load (preliminary force) of 1 N was applied and the end of test was determined to be the maximum extension (8.5 mm); the distance equivalent to 0.5 ml of gel (measured using Vernier's callipers). The speed of injection was defined as 2 ml/min or 1 ml/min. The hydrogel samples were then loaded to failure and the hydrogel expelled from the catheter was collected in a vial.

TABLE 3

Summary of medical devices used in injectability testing

| Medical Device | Needle Gauge (G)/ Catheter diameter (Fr) | Length (cm) |
|---|---|---|
| Cook Medical Needle | 18G | 7 cm |
| Chiba Biopsy Needle | 18G | 20 cm |

TABLE 3-continued

Summary of medical devices used in injectability testing

| Medical Device | Needle Gauge (G)/ Catheter diameter (Fr) | Length (cm) |
|---|---|---|
| Chiba Biopsy Needle | 20G | 10 cm |
| Terumo Spinal Needle | 23G | 9 cm |
| Cordis Catheter | 5Fr | 65 cm |

Example 15—Ultrasound and Computed Tomography (CT) Imaging 5 ml of iodinated contrast agent labelled polymer solution was injected into an ex vivo animal tissue (calf liver) model to assess distribution of injected ChemoGel in tissue. Prior to injection, the calf's liver was heated to 37° C. in a water bath. Internal tissue temperature was recorded using a meat thermometer. The polymer solution was injected using an 18G needle of 5 cm length (Cook Medical, Bloomington, Ind.) at a constant rate. Ex vivo distribution was imaged using Computed Tomography (Ingenuity Core 128, Philips). Images were obtained using 0.8 mm slice thickness, 0.4 mm reconstruction interval, 168mAs and 100 kV. A region of interest (100 mm diameter) within each well was selected and the average density was calculated (minimum, maximum and standard deviation also recorded).

Ultrasound images (Xario, Toshiba) were obtained using a 12 MHz linear probe in Grayscale B-mode.

Example 16—In-Vitro Cytotoxicity Assay

All cell culture was carried out in a class II laminar airflow cabinet, which was cleaned down with 70% Ethanol prior to, and following, use. All items entering the airflow cabinet were also swabbed with 70% Ethanol. UV sterilisation was used for at least 15 minutes prior to use of different cell line to avoid cross contamination. Cell lines were resurrected from storage in liquid nitrogen prior to use. The vial containing the cell line was defrosted quickly in a waterbath at 37° C., turning it often to minimise temperature gradients. Cell culture medium was added dropwise to the defrosted cells and this was centrifuged at 1200 rpm for five minutes at room temperature. The supernatant was aspirated off the pellet to remove any DMSO from the freezing medium and the cells were resuspended in supplemented cell culture medium and transferred to a T175 $cm^2$ flask (Starstedt, Ireland). Supplemented medium was replaced every three days and cells were passaged when they had reached 80-90% confluency (A549 cells and Panc-1 cells). Passaging of cells was carried out by removing all medium from the flask. Cells were detached from the flask by adding 5 ml of Trypsin to the flask and incubating at 37° C. for 5 minutes in a 5% $CO_2$, 90% humidity environment. The flask was then physically agitated to ensure complete detachment. 10 ms of supplemented medium was then added to the flask to stop the trypsinisation process and prevent cell death. This mixture was removed from the flask and added to a 50 ml Falcon Tube. The mixture was centrifuged at 1200 rpm for five minutes at room temperature. The trypsin:medium mixture was carefully discarded and the pellet of cells formed was then resuspended in fresh media.

For cytotoxicity assessment, cell viability was determined using the Cell Counting Kit-8 (CCK-8) colorimetric assay according to manufacturer's instructions. The CCK-8 assay uses a water-soluble tetrazolium salt (WST), WST-8, to quantify the cell viability. At the pre-determined timepoint, the appropriate treatment was discarded from the well, and the well was washed once with PBS. 200 uL fresh supplemented medium was added to each well. 20 uL of CCK-8 reagent was added to each well and the plates were returned to the incubator for 90 minutes or 3 hours for A549 cells or Panc-1 cells, respectively. 100 uL of the CCK-8 incubated medium was then transferred to a 96 well plate and absorbance was read at 450 nm on a Varioskan Flash Plate Reader. Medium treated cells were taken as 100% viability and the viability of each treatment group was expressed as a percentage of this.

Live/Dead staining was performed using a modified version of the manufacturers protocol (Invtirogen, Ireland) (Invitrogen, 2004). Live cells were stained green using Calcein AM and dead cells were stained red using Ethidium homodimer-1. 2.5 μL Calcein AM and 10 μL Ethidium homodimer-1 was added to 5 ml PBS. At the pre-determined timepoint, the appropriate treatment was discarded from the well and washed once with PBS. 300 μL of this Calcein AM/Ethidium homodimer-1 solution was added to each treatment well and allowed to develop for 30 minutes. The stains were then removed and 300 μL of PBS was added to the wells. Live and dead cells were visualised individually using blue (FITC/GFP) and green (RFP) filters respectively with a Leica DMIL microscope (Leica Microsystems, Switzerland). Image J was used to compile composite images of cell viability. Cytotoxicity protocols were based on methods published by Ma et al. (2014) (Ma et al., 2014). Cells were seeded at a density of 20,000 cells per well in a 24 well plate with 500 uL of supplemented medium. Cells were allowed to adhere for 24 hours at 37° C. in a 5% $CO_2$, 90% humidity environment. After 24 hours, medium was removed from wells, and replaced with fresh supplemented medium. Appropriate volumes of blank or drug loaded polymer solutions (0, 10, 20 or 30 uL) were added to the fresh supplemented medium to bring the final volume of each well to 500 uL. Plates were returned to the incubator at 37° C. in a 5% $CO_2$, 90% humidity environment for 24 or 48 hours. Following the pre-determined incubation period, the plates were removed from the incubator and the supernatant was discarded. The wells were washed once with PBS and the appropriate viability assay was carried out as outlined above.

Example 17—In-Vivo Studies

Hydrogel of Example 1 (GF5 hydrogel) was evaluated in two in vivo xenograft models, both lung cancer (A549 cells) and Pancreatic cancer (Panc-1 cells). Additionally hydrogel of Example 4 was evaluated in a lung cancer (A549 cells) xenograft model and hydrogel of Example 5 was evaluated in a Pancreatic cancer (Panc-1 cells) xenograft model. Successful establishment of both xenograft models was achieved, with tumours reaching required volume for experimentation three to six weeks post-injection.

All animal experiments were approved by the Animal Research Ethics Committee, Royal College of Surgeons in Ireland (REC no. 1389) and by the national scientific animal regulatory authority, the Health Products Regulatory Authority (HPRA) (Project authorisation: AE19127/P40), and were conducted in accordance with European Union legislation (Directive 2010/63/EU) on the subject of animal rights.

Tumour Xenograft Establishment

A bioluminescent A549-uciferase cell line and a non-bioluminescent Panc-1 cell line were used to establish the lung and pancreatic xenograft models respectively in Female Hsd:Athymic Nude-Foxn1nu mice (20-25 g weight). A549-luc or Panc-1 cells were trypsinised at 80-90% confluency, and resuspended in a PBS:Matrigel mixture (1:1) at a density of $1\times10^7$ cells/ml, and kept on ice until use, based on methods by Fridman et al. (2012). Once anaesthesia had been induced via inhalation using 4% v/v isoflurane and oxygen in an induction chamber, 2% v/v isoflurane used as maintenance anaesthesia in induction chamber or nose cone. 100 µL of cell suspension ($1\times10^6$ cells) was injected SC into the flank of the mouse in the lower right hand quadrant, using a 29G insulin syringe (Romed, Utrecht, Netherlands). The needle was left in place for 30 sec after injection, rotated and removed slowly to prevent leakage of cell suspension from injection site. Animals were then placed into a clean recovery cage adjacent to a heat lamp, and allowed to fully recover from anaesthesia before being returned to their home cage.

Intratumoural Injection

Intratumoural (IT) administration of sterile blank (Example 1,GF5) or drug-loaded hydrogel (Example 5 or Example 7) formulation or saline was undertaken once tumour volume had reached 250 mm$^3$±50 mm$^3$ for A549-uc xenografts and 170 mm$^3$±50 mm$^3$ for Panc-1 xenografts. A pre-determined volume (calculated based on tumour volume) of the hydrogel formulation or saline for injection was loaded into a 1 ml luer-lock syringe with 22G needle and kept on ice prior to administration. Inhalation anaesthesia was induced as per protocol. Tumours were stabilised using forceps and secured from beneath to minimise risk of needle piercing through tumour. The needle was inserted into the tumour, and the entire volume of required formulation was expelled slowly. The needle remained in place for 30 sec following completion of injection to allow for gelation of hydrogel formulations to occur, rotated and removed slowly to prevent backflow of injected material. Animals were then placed into a clean recovery cage adjacent to a heat lamp and allowed to fully recover from anaesthesia before being returned to their home cage.

Xenograft Monitoring

Once tumours were palpable, dimensions of the tumour were taken externally using digital callipers to measure the length (l) and width (w).

Tumour volume was derived using Equation 1 (Tomayko et al, 1989).

$$\frac{\text{length} \times \text{width}^2}{2} \qquad \text{(Equation 1)}$$

In vivo bioluminescent imaging was conducted when the A549-luc tumours had reached a volume of 250 mm$^3$±50 mm$^3$. Animals were injected IP with freshly prepared D-Luciferin solution in PBS (150 mg/kg) and anesthetised via inhalation as per protocol. Fluorescent imaging of the IT administered hydrogel formulations was also undertaken following incorporation of a fluorescent tag into the formulation. Ex vivo imaging was also carried out on the excised tumour tissue. Visualisation of the bioluminescent and fluorescent light emitted from the A549-luc cells and hydrogel formulations respectively using an IVIS@Spectrum In Vivo Imaging System was conducted using the parameters in Table 1.

Pseudo-coloured images of the bioluminescent and fluorescent signals were generated and superimposed on greyscale images of the whole animal or excised tissue by the Living Image software. Images were used for qualitative confirmation of hydrogel localisation and retention.

Off-Site Toxicity Assessment

General animal welfare was assessed by monitoring body weight throughout the study. Under deep systemic anaesthesia (ketamine (90 mg/kg) and xylazine (10 mg/kg) were administered IP using a 25G needle and 1 ml uer-lock syringe), terminal cardiac puncture was performed, using a 1 ml luer-slip syringe (B Braun, Melsungen, Germany) and 21G needle. The animal was placed securely on its back, and the needle was inserted at a 45 angle into the heart. The plunger was slowly withdrawn to collect the circulating blood, and needle was repositioned if required to complete blood collection, with due care given to prevent coagulation of blood in needle or syringe during procedure. 300 µL of the collected blood was then expelled into a K$_3$EDTA anti-coagulation tube (Microvette 500 K3E, Sarstedt, Numbrecht, Germany) and the remainder was expelled into a 2 ml Eppendorf tube (Eppendorf, Hamburg, Germany). The anti-coagulated blood sample in the K$_3$EDTA tube was analysed immediately for white blood cell count using a Sysmex KX-21N haematology analyser (Sysmex Corp., Kobe, Japan). The remaining blood sample was allowed to stand for approximately 30 min to coagulate. Samples were then centrifuged at 4,700 rpm for 5 min using a Minispin® centrifuge (Eppendorf, Hamburg, Germany) to separate out the blood serum. Serum was carefully removed from the centrifuged tube and transferred to a CryoPure Tube (Sarstedt, Numbrecht, Germany) and frozen at −80° C. until analysis. Serum was analysed using Aspartate Aminotransferase (AST) and Urea assay kits according to manufacturer's instructions. Absorbance was read at 450 nm and 570 nm respectively using a Victor$^2$ 1420 plate reader (Perkin Elmer, Mass., USA).

Following terminal cardiac puncture, death of the animal was confirmed using cervical dislocation. Liver and kidneys were identified and removed using a sharp scissors. The tumour was then removed from the lower right hand quadrant of the flank. All tissues collected at necropsy were placed in 10% neutral buffered formalin fixative solution for 24 h and then transferred to 70% ethanol. Formalin-fixed tissues were trimmed, processed and embedded into paraffin blocks. Representative 5-um thick sections from each individual paraffin-embedded tumors, kidneys and liver samples were prepared and stained with hematoxylin and eosin (H&E).

Figure 14A:
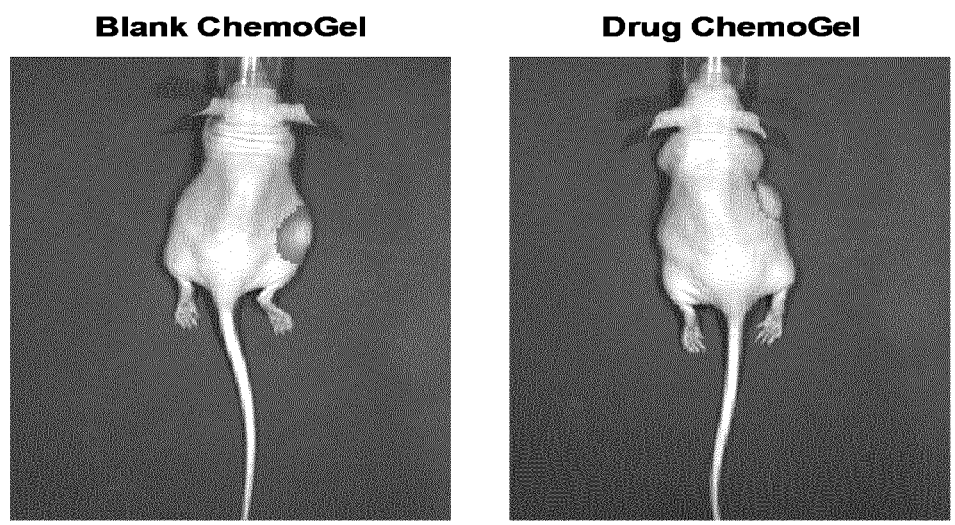
FIG. 14. Blank and drug hydrogel (Example 1 GF5 (Table 2), and Example 4) was retained at site of injection for 14 days in vivo (Example 17). (A) Representative overlay images of bioluminescent A549-luc cells post-intratumoural administration of 100 μL of fluorescently tagged hydrogel GF6 (left) or drug-loaded hydrogel (right) at Day 0. Blue represents bioluminescent signal from A549-luc cells, Yellow represents fluorescent signal from blank or drug hydrogel. (B) Representative fluorescent images at Day 0 (top) and Day 14 (bottom) post-intratumoural administration of saline (left), hydrogel (centre) or drug-loaded hydrogel (right). (C) Representative photographic (left) and fluorescent (right) images of excised tumours at Day 14 post intratumoural administration of saline (top) or hydrogel (bottom). Zoomed section indicates hydrogel macroscopically visible.
Figure 14B:
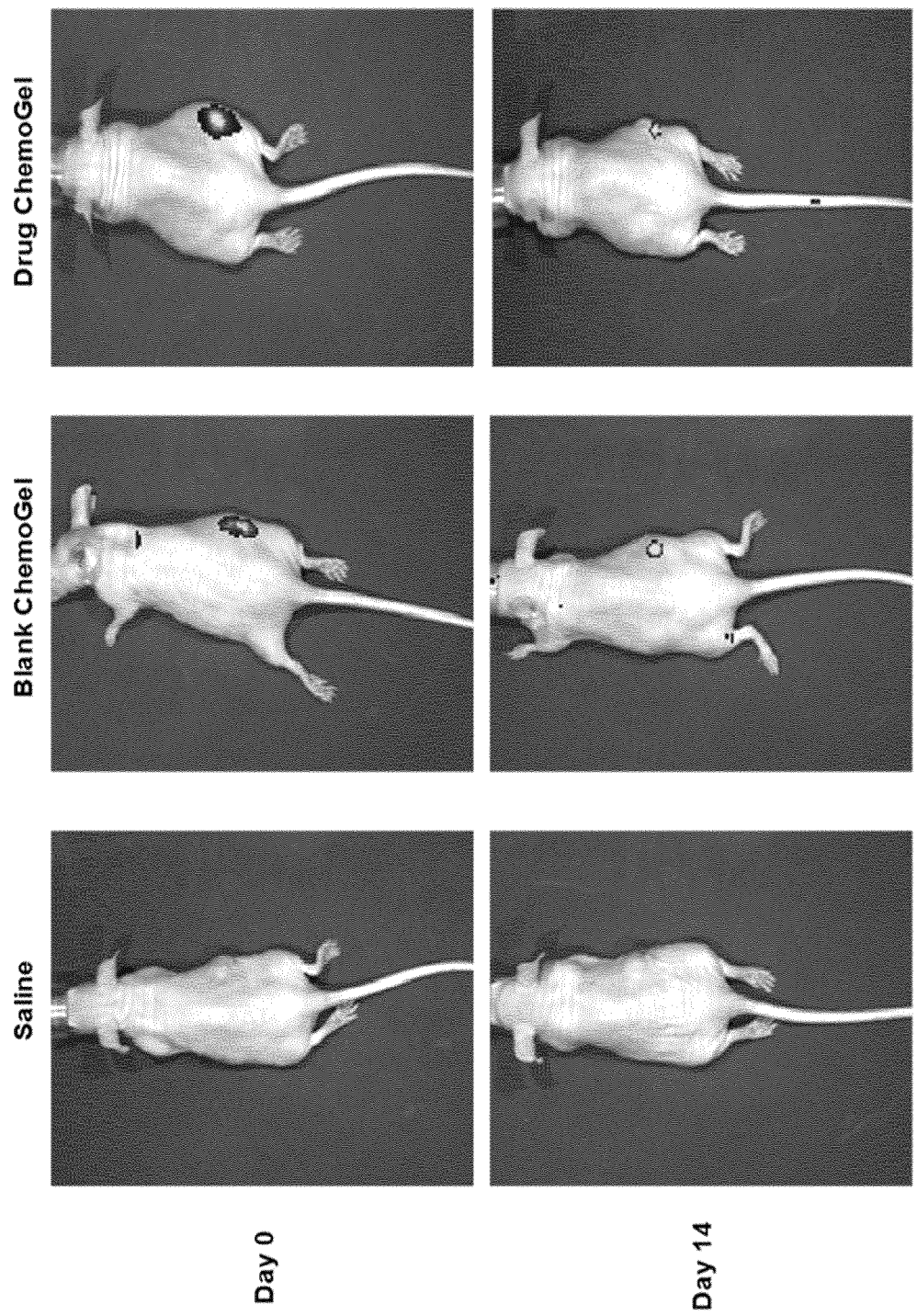
Figure 14C:
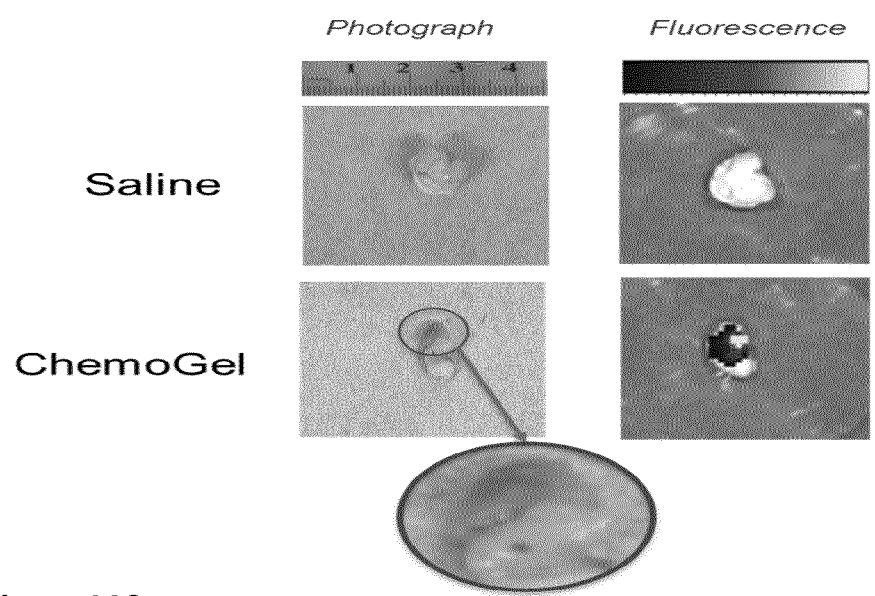

Evidence supporting the retention, efficacy and minimal off-site toxicity of hydrogel formulations of the invention administered to murine models of lung and pancreatic cancer has been determined. Results supporting the use of the hydrogel of the invention as a locoregional drug delivery platform in the treatment of solid tumours has established that intratumoural administration of the hydrogel:

Facilitated localised gelation at site of administration (FIG. 14A), with retention for at least 14 days (FIGS. 14B & 14C)

Figure 15:
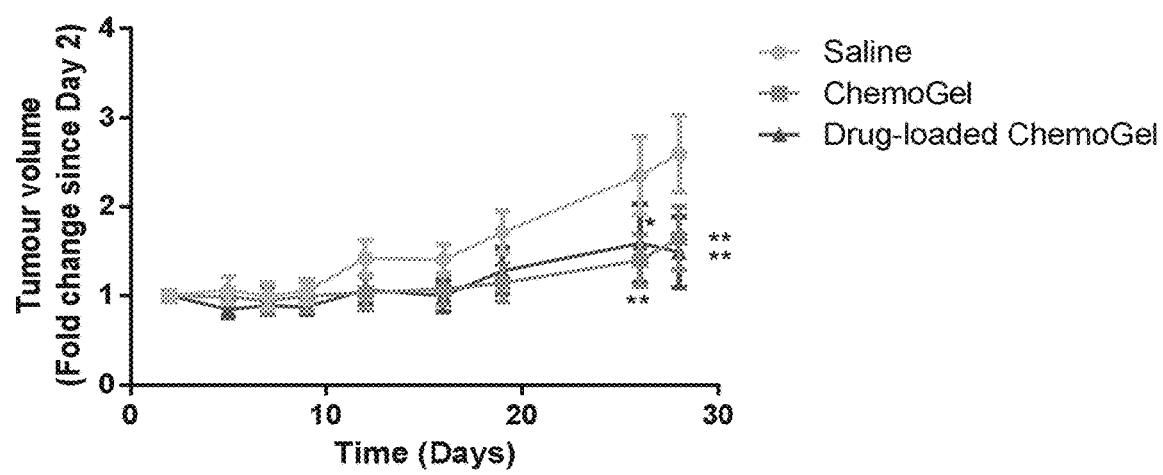
FIG. 15. Intratumoural administration (Example 17) of blank or drug-loaded hydrogel formulations (Example 1 GF5, and Example 5) significantly reduced tumour volume increase in a Panc-1 xenograft model. Tumour volume fold change following intratumoural administration of saline, hydrogel or drug-loaded hydrogel at Day 0. Data shown is represented as the mean±SEM (n=6-7 mice per group). Significance was determined using a repeated measures two-way ANOVA. *=$p<0.05$, **=$p<0.01$, compared to volume of blank or drug loaded ChemoGel tumour volume at the same timepoint.
Figure 17:
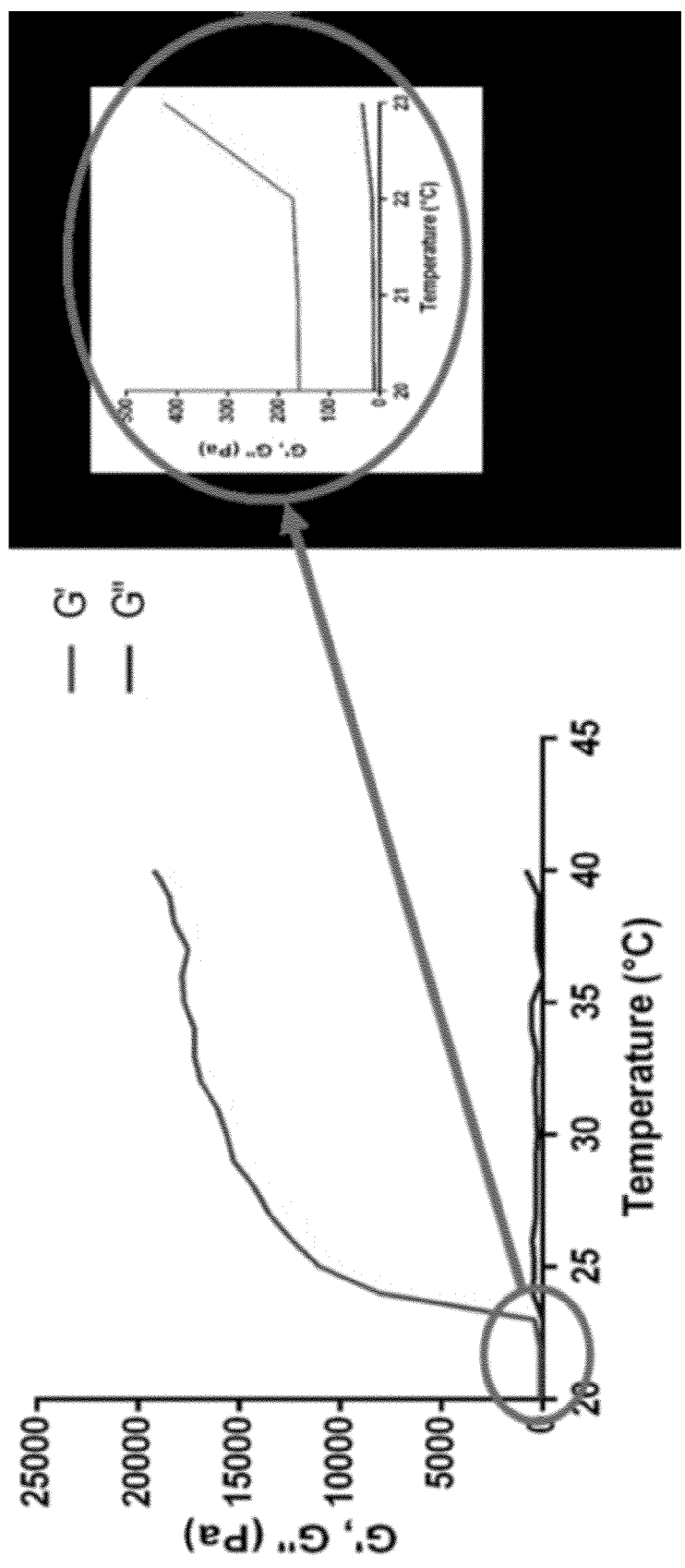
FIG. 17. Addition of Cisplatin to Jordan gel (GF1—Table 1) resulted in loss of the thermoresponsive nature at clinically relevant temperatures. Rheogram of temperature sweep of Jordan gel containing cisplatin from 20° C.–40° C. demonstrating that G'>G" at 20° C., depicted in the magnified segment of graph (green circle). Data shown is representative of the norm. G', storage modulus; G" loss modulus.
Figure 18:
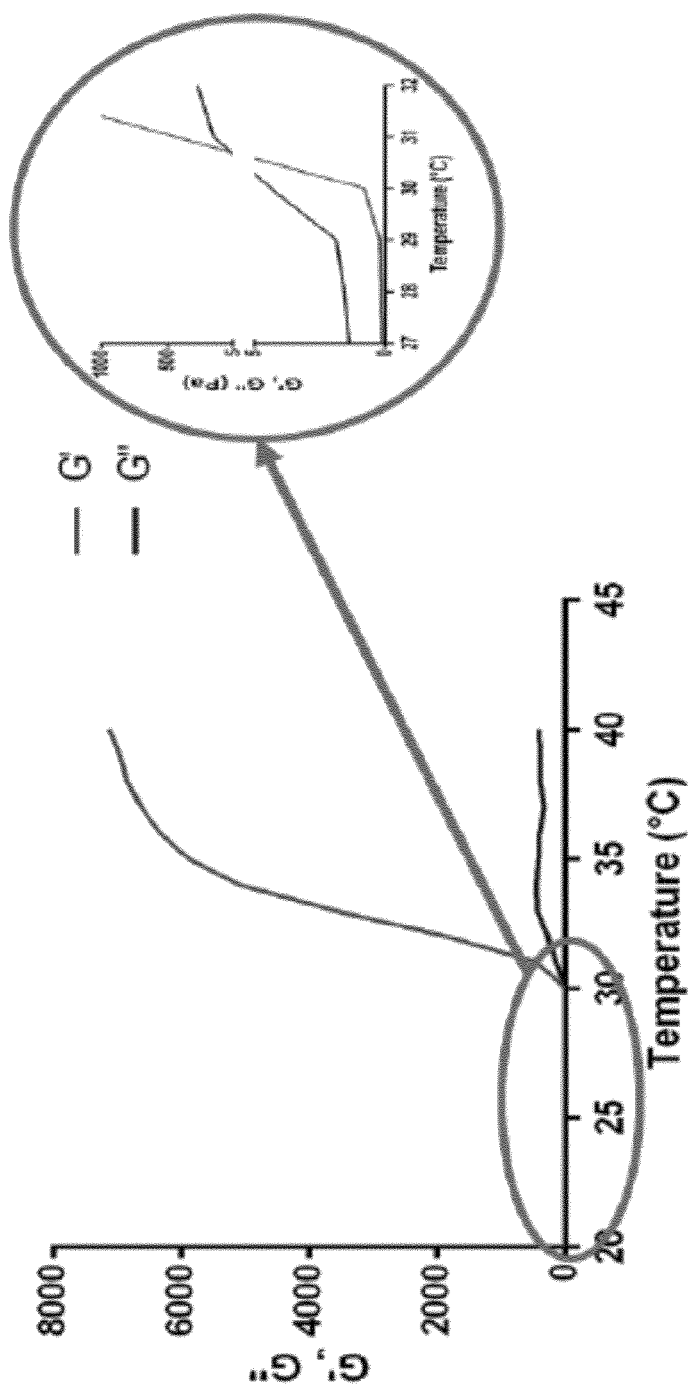
FIG. 18. Addition of cisplatin to a formulation of the invention (GF5—Table 1) produced a hydrogel showing thermoresponsivity in a clinically relevant range. Rheogram of temperature sweep demonstrates G'>G" at 31°, depicted in magnified segment of the graph. Data shown is representative of the norm.

Demonstrated efficacy in significantly reducing tumour volume increase in two different types of solid tumours over a period of 14-28 days (FIG. 15)

Does not induce acute off-site toxicity (FIG. 16).

EQUIVALENTS

The foregoing description details presently preferred embodiments of the present invention.

Numerous modifications and variations in practice thereof are expected to occur to those skilled in the art upon consideration of these descriptions. Those modifications and variations are intended to be encompassed within the claims appended hereto.

REFERENCES

Cho, H. J., Balakrishnan, P., Park, E. K., Song, K. W., Hong, S. S., Jang, T. Y., . . . Kim, D. D. (2011). Poloxamer/cyclodextrin/chitosan-based thermoreversible gel for intranasal delivery of fexofenadine hydrochloride. J Pharm Sci, 100(2), 681-691. doi: 10.1002/jps.22314

Fatimi, A., Chabrot, P., Berrahmoune, S., Coutu, J. M., Soulez, G., & Lerouge, S. (2012). A new injectable radiopaque chitosan-based sclerosing embolizing hydrogel for endovascular therapies. Acta Biomater, 8(7), 2712-2721. doi: 10.1016/j.actbio.2012.04.006 Invitrogen. (2004). LIVE/DEAD® Viability/Cytotoxicity Kit for Mammalian Cells Protocol. Retrieved 28 February, 2016, from https://www.thermofisher.com/ie/en/home/references/protocols/cell-and-tissue-analysis/protocols/live-dead-viability-cytotoxicity-kit-for-mammalian-cells.html Ma, H., He, C., Cheng, Y., Li, D., Gong, Y., Liu, J., . . . Chen, X. (2014). PLK1shRNA and doxorubicin co-loaded thermosensitive PLGA-PEG-PLGA hydrogels for osteosarcoma treatment. Biomaterials, 35(30), 8723-8734. doi: http://dx.doi.org/l0.1016/.iomaterials.2014.06.045

Jordon, K. (2012) An investigation of the cytotoxicity of a novel thermo-responsive gel for use in injectable intratumoral cancer therapy. The Undergraduate Journal, Volume 4, P286-309 https://issuu.com/undergraduateawards/docs/ua_journal_vol4_web.

Fridman, R., et al., Increased initiation and growth of tumor cell lines, cancer stem cells and biopsy material in mice using basement membrane matrix protein (Cultrex or Matrigel) co-injection. Nat Protoc, 2012. 7(6): p. 1138-44.

Tomayko, M. M. and C. P. Reynolds, Determination of subcutaneous tumor size in athymic (nude) mice. Cancer Chemother Pharmacol, 1989. 24(3): p. 148-54.

The invention claimed is:

1. A lyophilised hydrogel formed by lyophilising an uncured thermo-responsive hydrogel, the uncured thermo-responsive hydrogel comprising:
   15-25% poloxamer P407 optionally in combination with poloxamer P188 (w/w);
   0.1-1.0% chitosan (w/w);
   0.05-0.20% genipin (w/w);
   5-20% inclusion complexer (w/w); and
   an aqueous base.

2. The lyophilised hydrogel according to claim 1, in which the inclusion complexer is a β-cyclodextrin.

3. The lyophilised hydrogel according to claim 1, in which the uncured thermo-responsive hydrogel comprises 15-18% poloxamer P407 optionally in combination with poloxamer P188 (w/w).

4. The lyophilised hydrogel according to claim 1, in which the uncured thermo-responsive hydrogel comprises 0.05-0.15% genipin (w/w).

5. The lyophilised hydrogel according to claim 1, in which the uncured thermo-responsive hydrogel further comprises a chemotherapeutic agent or a combination of chemotherapeutic agents.

6. The lyophilised hydrogel according to claim 5, in which the chemotherapeutic agent is selected from cisplatin, paclitaxel, gemcitabine, a combination of cisplatin and paclitaxel, or a combination of gemcitabine and paclitaxel.

7. The lyophilised hydrogel according to claim 1, in which the uncured thermo-responsive hydrogel further comprises a contrast agent.

8. The lyophilised hydrogel according to claim 1, in which the uncured thermo-responsive hydrogel comprises about 0.1% genipin (w/w).

9. The lyophilised hydrogel according to claim 1, in which the uncured thermo-responsive hydrogel comprises:
   15-25% poloxamer P407 optionally in combination with poloxamer P188 (w/w);
   0.1-1.0% chitosan (w/w);
   0.05-0.15% genipin (w/w);
   5-20% 2-Hydroxypropyl β-cyclodextrin (w/w);
   a chemotherapeutic agent; and
   an aqueous base.

10. The lyophilised hydrogel according to claim 1, in which the uncured thermo-responsive hydrogel comprises:
   15-18% poloxamer P407 optionally in combination with poloxamer P188 (w/w);
   0.1-1.0% chitosan (w/w);
   0.05-0.15% genipin (w/w);
   5-20% 2-Hydroxypropyl β-cyclodextrin (w/w);
   a chemotherapeutic agent; and
   an aqueous base.

11. The lyophilised hydrogel according to claim 1, in which the uncured thermo-responsive hydrogel comprises:
   15-18% poloxamer P407 optionally in combination with poloxamer P188 (w/w);
   0.1-1.0% chitosan (w/w);
   0.05-0.15% genipin (w/w);
   5-20% 2-Hydroxypropyl β-cyclodextrin (w/w);
   a chemotherapeutic agent;
   a contrast agent; and
   an aqueous base.

12. The lyophilised hydrogel according to claim 1, in which the uncured thermo-responsive hydrogel has a storage modulus G' of at least 8,000 Pa at 37° C.

* * * * *